United States Patent [19]
Sprott et al.

[11] Patent Number: 5,989,587
[45] Date of Patent: Nov. 23, 1999

[54] FORMATION OF STABLE LIPOSOMES FROM LIPID EXTRACTS OF ARCHAEOBACTERIA (ARCHAEU)

[75] Inventors: G. Dennis Sprott, Ottawa; Girishchandra B. Patel, Nepean; Christian G. Choquet; Irena Ekiel, both of Quebec, all of Canada

[73] Assignee: National Research Council of Canada, Ottawa, Canada

[21] Appl. No.: 08/211,987

[22] PCT Filed: Oct. 23, 1992

[86] PCT No.: PCT/CA92/00464

§ 371 Date: Apr. 25, 1994

§ 102(e) Date: Apr. 25, 1994

[87] PCT Pub. No.: WO93/08202

PCT Pub. Date: Apr. 29, 1993

[51] Int. Cl.[6] .............................. A61K 9/127; C07C 59/00
[52] U.S. Cl. ...................... 424/450; 428/402.2; 554/79; 554/80; 554/213
[58] Field of Search ................... 424/450; 428/402.2; 554/79, 80, 213

[56] References Cited

U.S. PATENT DOCUMENTS

| | | | |
|---|---|---|---|
| 4,722,842 | 2/1988 | Stallcup | 424/95 |
| 5,098,588 | 3/1992 | Chang | 252/52 R |

FOREIGN PATENT DOCUMENTS

2050287  1/1981  United Kingdom.

OTHER PUBLICATIONS

Ferrante et al; Structures of polar lipids from the thermophilic...; Biochem. cell Biol. 68 1990; pp. 274 to 283.
Sprott et al; Novel, Acid–labile, Hydroxydiether Lipid Cores...; 1990; The Journal of Biological Chemistry vol. 265 —pp. 13735 to 13740.
Kushwaha et al; Novel polar lipids from the Methanogen...; Biochimica et Biophysica Acta, 664(1981) —pp. 156 to 173.
Lo, BBRC, 167 #1, 1990
Mirghani, Biochem. Soc. Transaction. 629th meeting, p. 507, 1989.
Woodle in Methods in Enzymol. 17, 1989 p. 193.
Biochimica et Biophysica Acta, 863 (1986) 213–223.
The Structure of membrane lipides of the extreme halophile, *Halobacterium cutirubrum*, P.J. Quinn et al.
Biochimica et Biophysica Acta, 352 (1974) 202–217, Osometric and Microscopic Studies on Bilayers of Polar Lipids of the Extreme Halophile, *Halobacterium Cutinebrum*, J. S. Chen et al.

*Primary Examiner*—Gollamudi S. Kishore
*Attorney, Agent, or Firm*—J. Wayne Anderson

[57] ABSTRACT

Novel ether lipids were obtained from methanogenic (*Methanospirillum hungatei, Methanococcus jannaschii, Methanococcus voltae, Methanosarcina mazei*, and *Methanobrevibacter smithii*), and extremely halophilic (*Halobacterium cutirubrum*) representatives of the archaeobacteria. Several of the ether lipids produced by *Methanospirillum* and Methanosarcina genera were purified and characterized structurally for the first time. Unilamellar liposomes were prepared from emulsions of the total polarether lipid extracts of such bacteria by pressure extrusion through membranes of various pore sizes. Liposome populations were shown by dynamic light scattering and electron microscopy to range in size depending on the pore size of the filter, on the source of the lipids, and on the composition of the suspending buffer medium. In all cases the size ranges indicated highly homogeneous preparations. Leakage of entrapped fluorescent or radioactive compounds esablished that the ether liposomes were stable to attack by phospholipase $A_2$ and B, and were stable for at least 60 days to storage in an atmosphere of air. The detergent dialysis method of forming liposomes also produced unilamellar liposomes from most of the archaeobacterial total polar lipid extracts which were tested.

32 Claims, 10 Drawing Sheets

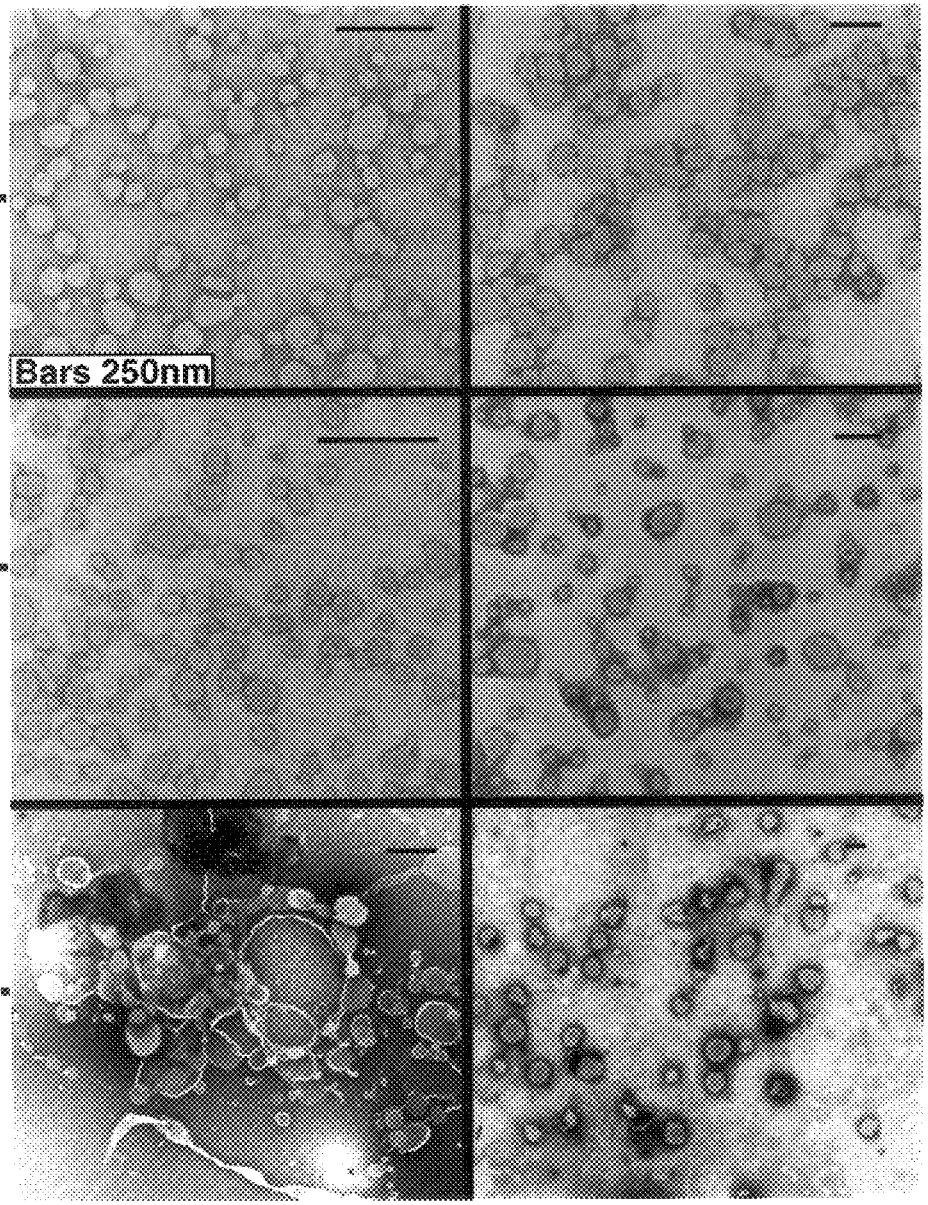

FORMATION OF STABLE LIPOSOMES FROM LIPID EXTRACTS OF ARCHAEOBACTERIA (ARCHAEU)

FIELD OF THE INVENTION

This invention relates to novel polyether lipids, to liposomes comprising polyether lipids, and to methods for producing such liposomes.

DESCRIPTION OF THE PRIOR ART

Artificial lipid vesicles (liposomes) have become an important tool in numerous basic and applied research areas. They have been used extensively as biological membrane systems for the study of such processes as transmembrane transport, lipid bilayer permeability, membrane fusion and lipid-protein interaction. They may also serve as immunological adjuvants or as carriers of drugs and skin care compounds, insecticides, genetic material and enzymes.

Currently, liposomes are made from ester-lipids, such as egg phosphatidylcholine (EPC). The inherent physicochemical instability of such liposomes is one of the major impediments to their commercial application. Accordingly, cholesterol is often included in the liposome composition to increase stability, decrease porosity, and prevent their fusion or aggregation. Moreover, the ester bonds of these liposomes are susceptible to enzymatic and chemical hydrolysis, which causes disruption of the liposome structure. Ester lipid fatty acyl chains are often unsaturated and therefore subject to oxidation in air and loss of the structural integrity of liposomes. A practically desirable shelf life of two years is normally not achieved and special storage conditions may be required, such as the removal of oxygen and/or lowered temperatures.

Archaeobacteria contain very different membrane lipid structures than their procaryotic and eucaryotic counterparts. Instead of fatty acyl chains, which are often unsaturated and are esterified to glycerol at carbons sn-1,2, archaeobacterial membrane lipids are composed of saturated phytanyl chains in ether linkage to glycerol carbons with sn-2,3 configuration. In addition to having the ubiquitous diether C20,20-lipid various methanogens can also have phytanyl chains modified to give rise to tetraether, hydroxydiether and macrocyclic diether lipids. Variations in the polar head groups are numerous and may provide a molecular taxonomic fingerprint for identification of each methanogen genus.

There are few reports of liposome formation from archaeobacterial lipids. Of these, one group reported on the formation of large liposomes, i.e. Ring, K. et al (1986) In Liposomes as Drug Carriers (Schmidt, K. H., ed), p. 101–123, Georg Thieme, Verlag, Stuttgart and New York. Specifically, Ring et al produced large vesicles (approximated as 600 nm) by controlled detergent dialysis of a single tetraether lipid component purified from the total lipid contents from the archaeobacterium *Thermoplasma acidophilum*. However, there is no teaching or suggestion of the application of this process to the production of liposomes from the total polar lipids of archaeobacteria. Also, these liposome structures were not defined by electron microscopy. Using the methods employed here with total polar and/or the total lipid extracts, we avoid the costly and difficult process of preparing purified lipid molecular species.

In another report by MacDonald, R. C. et al (1991) Biochim. Biophys. Acta 1061: 297–303, ester lipid liposomes are formed by pressure extrusion. However, there is no teaching of making unilamellar liposomes from the total polar lipid extracts of archaeobacteria. Because of the stability inherent in the archaeobacterial lipid structures it is possible to make liposomes over a wide range of conditions, including gas phase, temperature, and pH. These factors are central to their usefulness in industrial applications as is the stability of these liposomes to a variety of conditions. Moreover, the formation of liposomes within a broad range of conditions, is not the case for ester lipids.

Liposomes have been made by sonication from a subfraction of the ether lipids of *Sulfolobus acidocalcarius* [Elferinck et al. (1992) J. Biol. Chem. 267: 1375–1381].

SUMMARY OF THE INVENTION

It is an object of the invention to provide novel polyether lipids.

It is another object of the invention to provide liposomes of enhanced stability.

It is a further object of the invention to apply novel processes for the production of such liposomes.

According to one aspect of the invention, novel polyether lipids of structural formula I are provided.

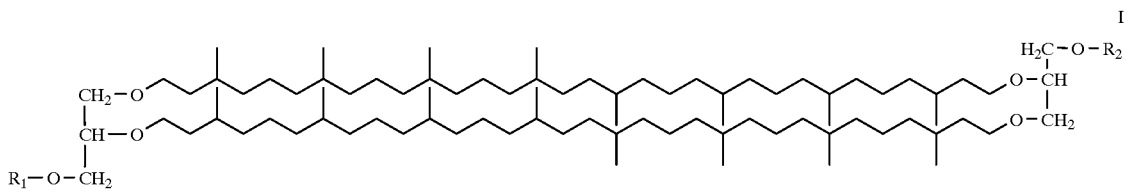

where $R_1$ is β-gal$_f$- and $R_2$ is α-glc$_p$- (1–2) - β-gal$_f$-

Additional novel polyether lipids are defined by structural formula II

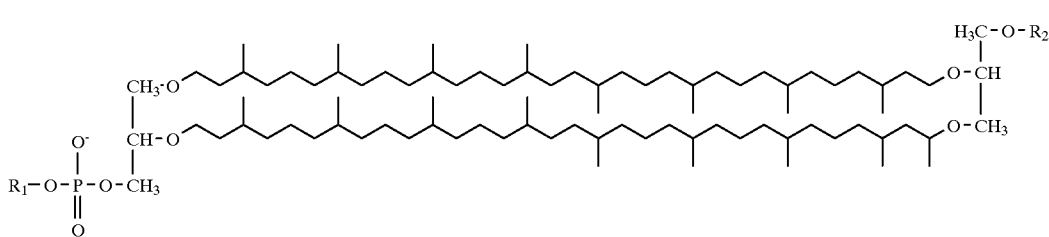

II where $R_1$ is $(CH_3)_2$-N—$C_5O_4H_{10}$— or $(CH_3)_3$-N—$C_5O_4H_{10}$— and $R_2$ is α-$glc_p$- (1–2) -β-$gal_f$- or β-$gal_f$-(1–6)-β-$gal_f$- or β-$gal_f$-.

Additional novel polyether lipids of structural formula III are also provided.

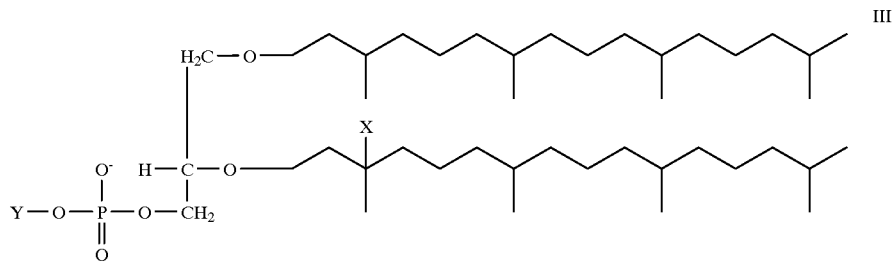

III wherein X is OH, and Y is ethanolamine or glycerol.

According to another aspect of the invention, liposomes prepared from the total polar lipid extract of various archaeobacteria are provided.

According to yet another aspect of the invention, a process for the production of unilamellar liposomes from the total polar lipid extracts of various archaeobacteria is provided, comprising
(a) subjecting cells of an archaeobacterium to solvent extraction to provide a total polar lipids fraction,
(b) adding a suitable detergent, in a molar ratio (detergent:lipid) ranging at least from 10:1 to 30:1, and removing the solvent completely by evaporation.
(c) dissolving the resulting detergent/lipid material in a suitable aqueous dialysis buffer to form mixed micelles of lipid and detergent, and
(d) subjecting the mixed micelles to controlled dialysis to remove the detergent, and form the liposomes. Preferably, in step (b), the detergent is a non-ionic detergent, for example, n-octyl-β-D-glucopyranoside, and the molar ratio (detergent: lipid) is about 20:1.

According to another embodiment of the Process, liposomes from the total polar lipids of archaeobacteria are provided by,
(a) subjecting cells of an archaeobacterium to solvent extraction to provide a total polar lipids fraction,
(b) adding a suitable aqueous extrusion buffer to form a multilamellar liposome emulsion at a pH range of 3.0 to 10.7, and where unilamellar liposomes are required,
(c) extruding the multilamellar liposome emulsion at a temperature of 4 to 80° C. under presssure through a membrane of selected pore size to form the unilamellar liposomes.

Preferably, for ease of operation, in step (c) the temperature is ambient.

BRIEF DESCRIPTION OF THE DRAWINGS

FIG. 1a is a continuation of FIG. 1 showing further lipid compounds according to the invention.

FIGS. 6A to 6F are a series of transmission electron microscope (TEM) photographs which illustrate the homogeneity of liposomes from the total polar lipid extracts of various archaeobacteria. Taking into consideration the size factor of 0.71, the bars equal 250 nm. (A) M. voltae; (B) M. jannaschii (65° C.); (C) M. mazei; (D) M. concilii; (E,F) M. hungatei -.

DETAILED DESCRIPTION OF THE PREFERRED EMBODIMENTS

As mentioned above, the archaeobacteria produce numerous different polyether lipid structures useful for the production of liposomes. Of the archaeobacteria available *Methanococcus voltae, Methanococcus jannaschii, Methanosarcina mazei, Methanospirillum hungatei, Methanosaeta concilii, Methanobrevibacter smithii, Methanosphaera stadtmanae, Thermoplasma acidophilum, Natronobacterium magadii,* and *Halobacterium cutirubrum* were chosen because their polar lipid compositions are very different from one another, and because they encompass the known spectrum of unusual core lipid structures found in archaeobacteria (See Table 1 and FIG. 1). Also, we demonstrate formation of liposomes from a wide range of archaeobacterial total polar lipid extracts. The archaeobacteria were chosen to encompass those which thrive in various harsh environments of low pH, high pH, high temperature, high salinity, and combinations thereof, with the expectation that liposomes formed from these sources would exhibit unusual stabilities. Further, the lipids were tested of archaeobacteria normally found in the human colon (*M. smithii,* and *M. stadtmanae*), since these liposomes may be especially relevant in development of drug delivery systems.

Figure 1:
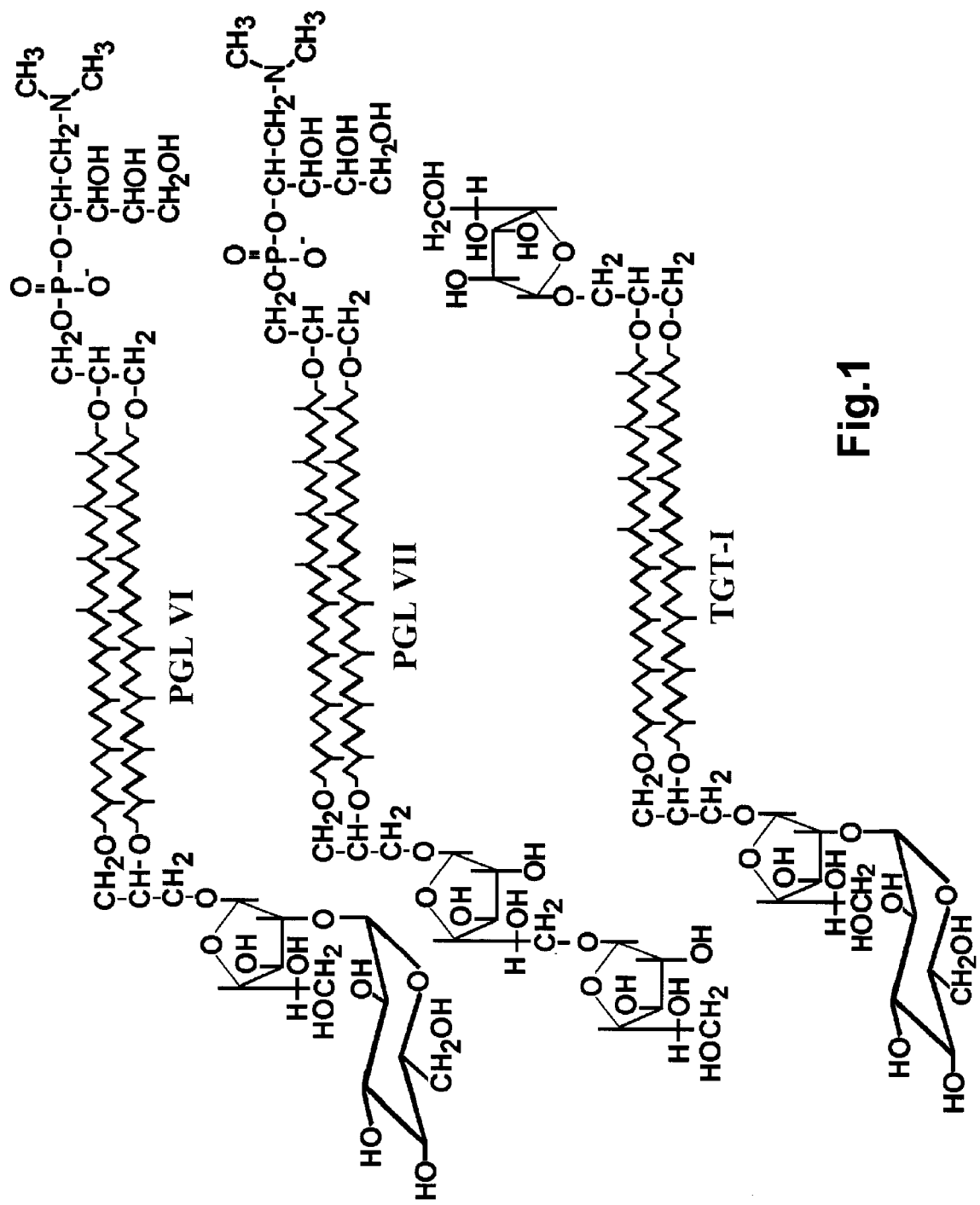
FIG. 1 is an illustration of the various structural formulae of the novel polyether lipid compounds from M. hungatei according to the invention.
Figure 1:
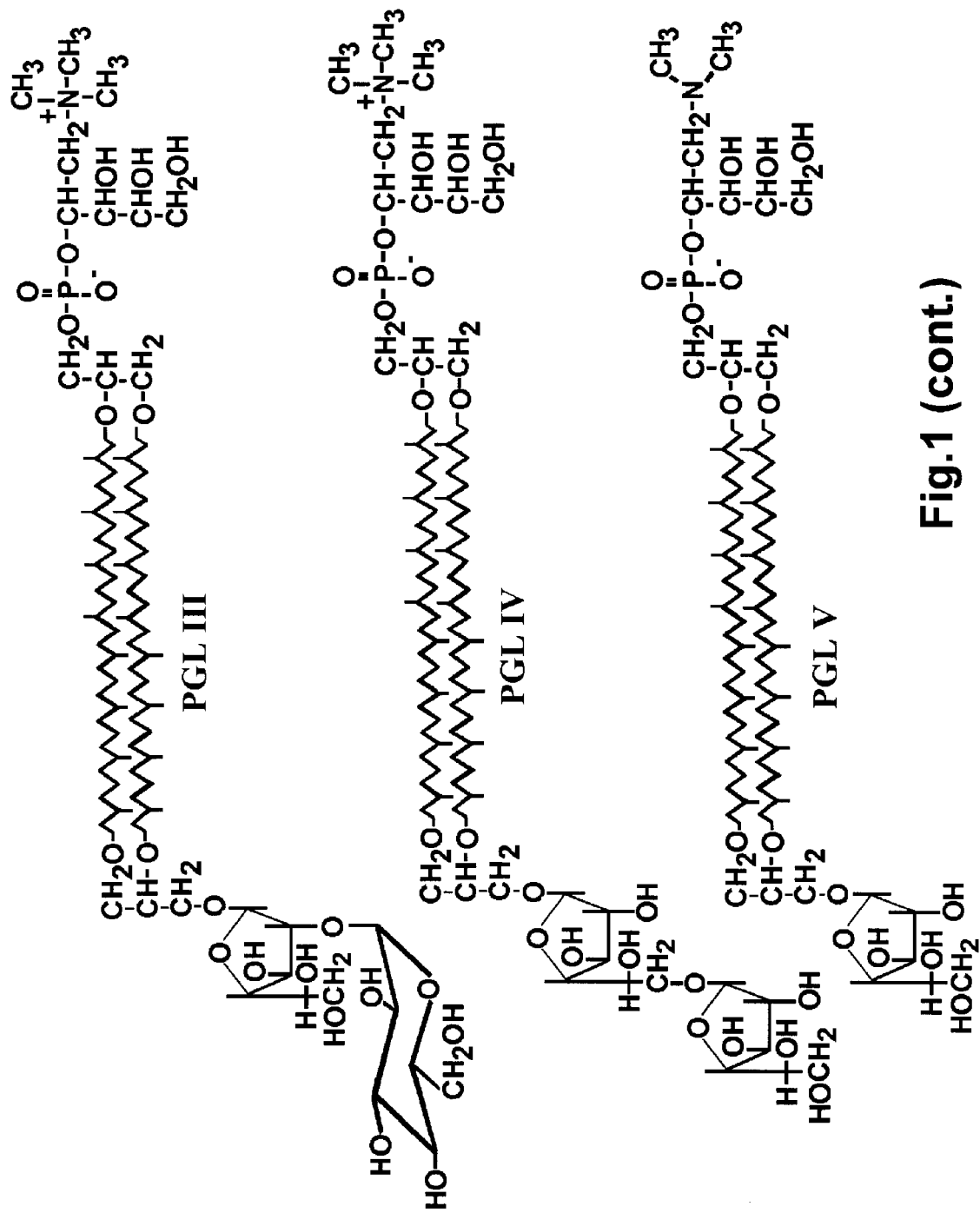

Novel lipid compounds have been isolated and characterized from *M. hungatei* and *M. mazei.* The structures of the novel compounds are illustrated in Formula I, II and III and FIGS. 1 and 1a.

*Methanosphaera stadtmanae* MCB-3 (NRC 6540=DSM 3091), *Methanobacterium espanolae* GP9 (NRC 5912=DSM 5982), *Natronobacterium magadii* (NRC 6561=ATCC 43099), *Halobacterium cutirubrum* (NRC 34001=DSM 669) and *Thermoplasma acidophilum* 122-1B3 (NRC 6566=ATCC 27658).

Methanogens were cultivated anaerobically as follows. *M. hungatei* was grown at 35° C. in an atmosphere of $H_2/CO_2$ (80:20, v/v) in SA medium [Breuil, C. and Patel, G. B. (1980) Can. J. Microbiol. 26: 577–582] supplemented with 5 μM $NiCl_2$. *M. stadtmanae* was cultured on methanol (0.1%, v/v) and $H_2/CO_2$ (80:20, v/v) at 35° C. in a medium originally described by Miller and Wolin [Miller, T. L. and Wolin, M. J. (1985) Arch. Microbiol. 141: 116–122] but that was modified by replacing the vitamin-free casein hydrolysate with 1 mM each of L-leucine and L-isoleucine, and by raising the nitrilotriacetic acid concentration to 30 mg/L and the $CaSO_4$-$5H_2O$, $H_3BO_3$ and $Na_2MoO_4$-$2H_2O$ concentrations to 200 μg/L. *M. smithii* was grown at 35° C. under $H_2/CO_2$ (80:20, v/v) in Balch medium-1 [Balch, W. E. et al., (1979) Microbiol. Rev. 43: 260–296] modified to include 0.1% (w/v) $NH_4Cl$, and HSCoM and fatty acids as in *M. stadmanae* medium. *M. concilii* was grown at 35° C. under $N_2$ in acetate medium [Ferrante, G., et al., (1989) J. Lipid Res. 30: 1601–1609]. Growth of *M. jannaschii* was conducted at either 50, or 65° C. under $H_2/CO_2$ (80:20, v/v) in defined medium [Ferrante, G. et al., (1990) Biochem. Cell Biol. 68: 274–283]. *M. voltae* was grown in an $H_2/CO_2$ atmosphere in Balch medium-3 [Balch, W. E. et al. (1979)

TABLE 1

Known distribution (%) of the different ether core lipids present in the archaeobacteria used in this study

| | $D_S$ | $D_{OH}$ | T | $D_M$ | References |
|---|---|---|---|---|---|
| METHANOGENS | | | | | |
| *M. voltae* | >90 | <10 | | | I. Ekiel, Dicaire, C., Patel, G. B., Choquet, C. G. and Sprott, G. D. unpublished data. |
| | | | | | Sprott, G. D., et al. (1990) J. Biol. Chem. 265: 13735–13740 |
| *M. concilii* | 70 | 30 (sn-3) | | | Ferrante, G., et al. (1988) Biochim. Biophys. Acta 963: 173–182 |
| *M. mazei* | 43 | 57 (sn-2) | | | Sprott, G. D., et al. (1990) J. Biol. Chem. 265: 13735–13740 |
| *M. hungatei* | 50 | | 50 | | Meloche, M. and Sprott, G. D., unpublished data. |
| *M. jannaschii* | | | | | |
| grown at 65° C. | 15 | | 42 | 43 | Sprott, G. D., et al. (1991) J. Bacteriol. 173: 3907–3910. |
| grown at 50° C. | 60 | | 21 | 19 | Sprott, G. D., et al. (1991) J. Bacteriol. 173: 3907–3910. |
| *M. smithii* | + | | + | | |
| *M. stadtmanae* | + | | + | | |
| *M. espanolae* | + | | + | | |
| EXTREME HALOPHILES | | | | | |
| *H. cutirubrum* | 100 | | | | Kates, M. (1978) Prog. Chem. Fats other lipids 15: 302–342 |
| *N. magadii* | 100 | | | | Langworthy, T. A., et al. (1982) Zbl. Bakt. Hyg., I. Abt. Orig. C3: 228–244 |
| THERMOACIDOPHILES | | | | | |
| *T. acidophilum* | 10 | | 90 | | Langworthy, T. A., et al. (1982) Zbl. Bakt. Hyg., I. Abt. Orig. C3: 228–244 |

Abbreviations: $D_S$, standard diether; $D_{OH}$, hydroxydiether; T, tetraether; $D_M$, macrocyclic diether; +, present but the amount has not yet been determined.

MATERIALS AND METHODS
SOURCE AND GROWTH OF BACTERIA

Bacterial cultures were *Methanospirillum hungatei* GP1 (NRC 2214=DSM 1101), *Methanosaeta concilii* GP6 (NRC 2989=DSM 3671), *Methanococcus jannaschii* JAL-1 (NRC 5952=DSM 2661), *Methanococcus voltae* PS (NRC 2854), *Methanosarcina mazei* S-6 (NRC 6052=DSM 2053), *Methanobrevibacter smithii* ALI (NRC 6539=DSM 2375), Microbiol. Rev. 43:260–296] at 35° C. Modified Balch-3 medium (in which yeast extract and tryptone were replaced by 0.1 g of L-isoleucine per liter and 0.05 g of L-leucine per liter, the $NH_4Cl$ concentration was raised to 0.54 g per liter, and $NaCO_3$ was replaced by $NaHCO_3$) was used to grow *M. mazei* on methanol under $N_2$. *M. espanolae* was grown on $H_2/CO_2$ at pH 5.0 in SA medium [Patel, G. B. et al. (1990) Int. J. Syst. Bacteriol. 40: 12–18].

*H. cutirubrum* was grown aerobically at 35° C. in defined medium (Grey and Fitt, 1976). *N. magadii* was grown aerobically at 37° C. at pH 9.0 in medium #1590 (ATCC catalogue 1989). *T. acidophilum* was grown aerobically at pH 2.0 and at 55° C. in medium #158 of the 1989 DSM (German Collection of Microorganisms and Cell Cultures) catalogue, but with the yeast extract concentration increased to 0.2% (w/v).

Mass cultivation for lipid recovery was in a 75 L Chemap AG fermentor in 55 L of fresh medium. Methanogen media were reduced with cysteine-sodium suphide [Hungate, R. E. (1950) Bacteriol. Rev. 14: 1–49]. The dissolved sulphide was maintained at 0.1 mM with the addition of agueous $Na_2S$. Extreme halophiles were supplied with 26 L of air/min and agitated at 150 rpm during growth. Cells were harvested in mid to late exponential growth and stored as a paste at −20° C. prior to lipid extraction.

LIPID EXTRACTION AND PURIFICATION

Total polar lipid extracts. Cells (100 g wet weight) were thawed and mixed overnight at 23° C. in chloroform/methanol/water (250 ml:500 ml:200 ml). Cell debris was removed by centrifugation and extracted twice more, as above. Extracts were pooled and lipids recovered from the chloroform phase as described [Bligh, E. G. and Dyer, W. J. (1959) Can. J. Biochem. Physiol. 37: 911–917]. The chloroform phase was concentrated by rotary evaporation to about 50 ml and the extraction repeated.

Polar lipids were recovered by dissolving the total lipid fraction in chloroform/methanol (2:1, v/v) and precipitated with 20 volumes of cold acetone [Ferrante, G. et al (1990) Biochem. Cell. Biol. 68: 274–283]. Lipid samples for use in liposome preparations were precipitated twice more and the lipids, once re-dissolved in chloroform/methanol (2:1, v/v), were further purified on a silica G column (2×5 cm). The lipids, eluted with 125 ml of 2:1 (v/v) chloroform/methanol followed by 125 ml of 1:2 (v,v) chloroform/methanol, were concentrated by rotary evaporation.

Purification of lipids. For structural characterization ether lipids were purified from *M. hungatei* and *M. mazei* polar lipid extracts using thin-layer chromatography (TLC) [Ferrante, G., et al. (1987) Biochim. Biophys. Acta 921: 281–291]. Purity was confirmed by thin-layer chromatography, mass spectrometry, and $^{13}C$ NMR spectrometry.

Lipids on TLC plates were stained for vic-glycols, phosphatides, carbohydrate, and amino groups (Ferrante, G., et al., 1987).

Polar head groups were removed by 0.18% methanolic HCl hydrolysis and the liberated core lipids purified by TLC [Sprott, G. D., et al. (1990) J. Biol. Chem. 265:13725–13740]

Phosphate was measured according to Allen [Allen, R. L. J. (1940) Biochem. J. 34: 858–865] and % C/H/N by elemental analysis.

Physical methods. Chemical ionization (CI) and FAB mass spectrometry were performed with a JEOL (JMS-AX505H) instrument. Optical rotation measurements of lipids dissolved in chloroform were obtained with a Perkin Elmer 243 polarimeter at room temperature. $^{13}C$ NMR spectra were run at 125 MHz, room temperature, using an AM500 spectrometer and lipids dissolved in $CDCl_3$ solution for core lipids or benzene-d6-methanol-d4 (7:1, v/v) for polar lipids.

LIPOSOME FORMATION BY DETERGENT DIALYSIS

Lipid/detergent mixed micelle formation. Polar lipids (40 mg) and n-octyl-β-D-glucopyranoside (OBG) were dissolved in $CHCl_3$ (2 mL). The detergent was added in a 20:1 molar ratio (OBG:lipid) assuming an average molecular weight of 1000 for the polar lipid extracts [Ferrante, G., et al. (1990) Biochem Cell. Biol. 68: 274–283]. The lipid/detergent solution was evaporated to dryness under $N_2$ and placed in vacuo overnight to remove all traces of $CHCl_3$. The mixed micelles were formed by dissolving the lipid/detergent material in 3 mL of dialysis buffer [10 mM K-phosphate buffer (pH 7.14) containing 160 mM NaCl]. Trace amounts of undissolved material were removed by filtration through a 0.22 μm nylon filter.

Liposome formation. The liposomes were formed by controlled dialysis of the lipid/detergent mixed micelles at room temperature with a Liposomat (Avestin Inc, Ottawa, Canada), operating for 4 h at a flow rate of 0.5 mL/min for the mixed micelles and 2.5 mL/min for the dialysis buffer.

Determination of the internal volume. The internal volume was determined with the marker [$^{14}C$ (U) ]sucrose (NEN Research Products, Mississauga, Ontario, Canada). Mixed micelles and liposomes were formed with dialysis buffer containing 0.3 mCi/L [$^{14}C$]sucrose. Thus, the concentration of [$^{14}C$]sucrose trapped inside the liposomes was the same as outside the vesicles. The specific activity of the [$^{14}C$]sucrose (4.2 mCi/mmol) was used to calculate the intravesicular aqueous compartment and these were expressed as μl of aqueous trapped volume per mg of total polar lipid following removal of free [$^{14}C$]sucrose.

The separation of free from entrapped sucrose was done on Sephadex G-50 (medium) columns using the microcolumn centrifugation method described by New [New, R.C.C. (1990) in Liposomes. A practical approach, pp. 105–162, IRL Press, Oxford]

Thin layer chromatography. Polar lipids were separated in chloroform/methanol/acetic acid/water (85:22.5:10:4, v/v) on Silica gel G plates (0.25 mm) and visualized by spraying the plates with a ceric sulfate/ammonium molybdate reagent (1 g $H_4(CeSO_4)_4$/2.5 g $(NH_4)_6Mo_7O_{24} \cdot 4H_2O$/10 ml $H_2SO_4$/90 ml $H_2O$) followed by heating at 100° C. [Ross, N. W. et al. (1991) FEMS Microbial. Lett. 81: 257–267].

Polar lipid and micellar extracts, both in $CHCl_3/CH_3OH$ (2:1, v/v), were applied directly to the TLC plates, while samples (5 mg) of the liposome suspensions were dried under $N_2$ and dissolved in $CHCl_3/CH_3OH$ (2:1, v/v) prior to their application to the plates.

LIPOSOME FORMATION BY PRESSURE EXTRUSION

The liposomes were formed by pressure extrusion according to MacDonald et al. [Macdonald, R. C. et al. (1991) Biochim. Biophys. Acta 1061: 297–303] using a LiposoFast (Avestin, Inc., Ottawa, Ontario, Canada). Unless otherwise stated, the lipids were homogenized [2 mL-size Potter-Elvehjem tissue grinder (Fisher Scientific)] in extrusion buffer [10 mM K-phosphate buffer (pH 7.14) and 160 mM NaCl] at a final concentration of 20 mg/mL. The resulting multilamellar liposomes were subjected to 21 passages through two (stacked) polycarbonate filters (19 mm diameter) of pore diameters of either 50, 100, 200 or 400 nm. With the exception of DPPC vesicles (50° C.) and unless otherwise stated, the liposomes were routinely formed at room temperature.

To study the effect of Ph on liposome formation, 25 mM citrate/phosphate (pH 3.0), or K-phosphate (pH 7.14 or carbonate/bicarbonate (pH 10.7) buffers containing 160 mM NaCl were used. Filters of 100 nm pore size were used for extrusion.

For the encapsulation of 5(6)-carboxyfluorescein (CF) and [$^{14}C$]sucrose, these were added to the extrusion buffer at concentrations of 100 mM and 150 mM (33 nCi/μmole), respectively. At that concentration CF is self-quenching and does not fluoresce but as it leaks out it is diluted and fluorescence becomes detectable. The separation of free from entrapped material was done on Sephadex G-50 (medium) columns using the microcolumn centrifugation method described by New [New, R.C.C. (1990) in Liposomes. A practical approach, pp. 105–162, IRL Press, Oxford.]

CHARACTERIZATION OF LIPOSOMES

Size determination. The mean diameter and the number-weighted size distribution of the vesicle preparations were determined by dynamic light scattering (DLS) using the NICOMP submicron particle sizer, model 370 (Nicomp, Santa Barbara, Calif., USA) and by direct measurements from electron micrographs of negatively stained preparations [New, R.C.C. (1990)].

Negative stains were prepared using Formvar carbon-coated copper grids (200 mesh) and a 1% solution of sodium phosphotungstate (pH 7.2). For a better dispersion of the liposomes, the grids were treated with bacitracin (0.1 mg/mL) [Gregory, D. W. and Pirie, B. J. S. (1973) J. Microscopy 99: 261–265] for 2 min prior to sample application. A drop of the proper liposome dilution ($10^{-1}$ to $10^{-2}$), using phosphotungstate as the diluant, was placed on the grid for 5 min and the excess stain drawn off with filter paper. The grids were observed with a Siemens 101 transmission electron microscope at 60 kV. To account for the flattening of the liposomes, the diameter of the measured disks were multiplied by 0.71 to approximate the diameter of the original liposomes [New, R.C.C. (1990)]. Lamellarity. The lamellarity of the liposomes were etermined by freeze fracturing. The liposomes were centrifuged at 200,000× $g_{max}$ for 5 h and the pellet distributed into gold freeze-etching planchets. These were frozen by plunging into propane held at liquid nitrogen temperature. The frozen material was fractured and etched (etching time of 30 s) in a Balzers BA 360 freeze-etcher equipped with electron guns as evaporation sources. The platinum-carbon replicas were cleaned of liposomal debris by treatment in concentrated sulphuric acid, 5% (W/V) sodium hypochlorite, and distilled water. The replicas were mounted on 400-mesh copper grids and viewed with a Philips EM 300 operating at 60 kV under standard conditions with the cold finger in place.

Stability testing: phospholipases. The activity of phospholipases $A_2$, B and C on liposomes were monitored by fluorescence spectroscopy [New, R.C.C. (1990)]. The reaction mixtures (1 ml) contained 5(6)-carboxyfluorescein (CF)-loaded liposomes and 50 units of phospholipase $A_2$ in a 50 mM carbonate/bicarbonate buffer (pH 8.9) or 10 units of phospholipase B in a 50 mM Na-phosphate buffer (pH 8.2) or 10 units of phospholipase C in a 50 mM Na-phosphate buffer (pH 7.14). The mixtures were incubated at 37° C. and the release of CF was followed as an increase in fluorescence.

Stability testing: temperature. The release of entrapped CF at different incubation temperatures was followed by fluorescence spectroscopy. CF-loaded liposomes resuspended in 10 mM K-phosphate/160 mM NaCl buffer were incubated at 4, 23, 35, 50 and 65° C. and the fluorescence measured at different time intervals. The amount of CF-loaded liposomes used in these assays were such that 100% release of CF, upon lysis with 0.2% Triton X-100, yielded a fluorescence equivalent to 20 $\mu$M CF. The fluorescence was monitored with a Farrand Spectrofluorometer MK-1 (Farrand optical Co., Inc., New York) set at an excitation wavelength of 470 nm and an emission wavelength of 520 nm.

Stability testing: leakage of [$^{14}$C]sucrose. The leakage of entrapped [$^{14}$C]sucrose during storage was monitored by determining the remaining percent radioactivity associated with the liposomes. Free [$^{14}$C]sucrose in aliquots (50 $\mu$l) of liposome suspensions was separated from entrapped [$^{14}$C] sucrose as described above and the radioactivity of the resulting liposomes counted in a LKB Wallace (model 1217 Rackbeta) liquid scintillation counter. The extent of entrapment (considered 100%) was determined within minutes following the formation of the liposomes.

Stability testing: vesicle size. The stability of the prepared liposomes, i.e. fusion and aggregation, was monitored periodically by DLS [Frokjaer, S., et al. (1984) in Liposome technology (Gregoriadis,G., ed.) vol 1, pp. 235–245, CRC Press, Inc., Boca Raton, Fla.].

RESULTS

LIPID STRUCTURES

*Methanospirillum hungatei*. Ether lipids uncharacterized in previous studies [Kushwaha, S. C., et al. (1981) Biochim. Biophys. Acta 664: 156–173; Ferrante, G., et al. (1987) Biochim. Biophys. Acta 921: 281–291] were purified from *M. hungatei* and found to be structurally novel (FIG. 1). The $R_f$ values and staining reactions are shown in Table 2 for the purified lipids separated on TLC using as solvent chloroform/methanol/acetic acid/water (85:22.5:10:4, v/v). Staining reactions are in keeping with the previous data and with the new structures PGL-III to PGL-VII and TGT-I. PGL-III to PGL-VI were phosphoglycolipids exhibiting a strong positive Dragendorff reaction for PGL-III and IV (typical of a N,N,N-trimethyl group) and a weak positive Dragendorff reaction (typical of a N,N-dimethyl group) in the case of PGL-V and PGL-VI.

TABLE 2

Relative abundance and staining characteristics of the ether lipids from *M. hungatei*

| Component | wt(%)[a] | $R_f$ value | Staining reaction[b] | | | |
|---|---|---|---|---|---|---|
| | | | Phosphate | Sugars | vic-glycols | Dragendorff |
| PGL-I | 23.7 | 0.14 | ++ | ++ | ++ | − |
| PGL-II | 3.9 | 0.18 | ++ | ++ | ++ | ± |
| PGL-III | 1.4 | 0.07 | ++ | ++ | ++ | ++ |
| PGL-IV | 0.5 | 0.09 | ++ | ++ | ++ | ++ |
| PGL-V | <0.5 | 0.33 | ++ | ++ | ++ | + |
| PGL-VI | 0.7 | 0.14 | ++ | ++ | ++ | ± |
| PGL-VII | 2.4 | 0.18 | | Not determined | | |
| TGT-I | <0.5 | 0.35 | | Not determined | | |
| DGD-I | 32.2 | 0.53 | − | ++ | ++ | − |

TABLE 2-continued

Relative abundance and staining characteristics of the ether lipids from *M. hungatei*

| Component | wt(%)[a] | $R_f$ value | Staining reaction[b] | | | |
|---|---|---|---|---|---|---|
| | | | Phosphate | Sugars | vic-glycols | Dragendorff |
| DGT-I | 12.5 | 0.61 | - | ++ | ++ | - |
| DGD-II | 2.0 | 0.65 | - | ++ | ++ | - |
| DGT-II | 0.9 | 0.70 | - | ++ | ++ | - |
| PPDAD | 9.7 | 0.51 | ++ | - | ++ | + |
| PPTAD | 8.9 | 0.31 | ++ | - | ++ | ++ |

[a]Represents the weight as % of total lipids recovered following purification
[b]Staining reactions determined for isolated lipids. ±, uncertain reaction.

Analytical data shown for glycolipids I, II, and III show an elemental analysis entirely in keeping with the predicted structures (Table 3.). Molecular weights of lipids containing the N,N,N-trimethylaminopentanetetrol are detected in negative FAB as the dimethyl forms [Ferrante, G., et al., (1987)], but are readily identified in both positive-FAB MS and NMR analysis.

TABLE 3

Analytical data for phosphoglycolipids I, III and IV

| | PGL-I | | PGL-III | | PGL-IV | |
|---|---|---|---|---|---|---|
| Element | Theoretical | Found | Theoretical | Found | Theoretical | Found |
| C | 68.03 | 68.17 | 67.56 | 67.66 | 64.98 | 67.66 |
| H | 11.16 | 11.70 | 11.15 | 11.22 | 10.66 | 11.22 |
| P | 1.79 | 1.74 | 1.62 | 1.65 | 1.60 | 1.65 |
| M | — | — | 0.72 | 0.75 | 0.77 | 0.75 |
| mol. wt | 1778.4 | 1778.8[a] | 1880.5 | 1864.1[a,b] | 1880.5 | 1864.1[a,b] |

[a]Negative-FAB MS
[b]Loss of methyl group

Figure 2:
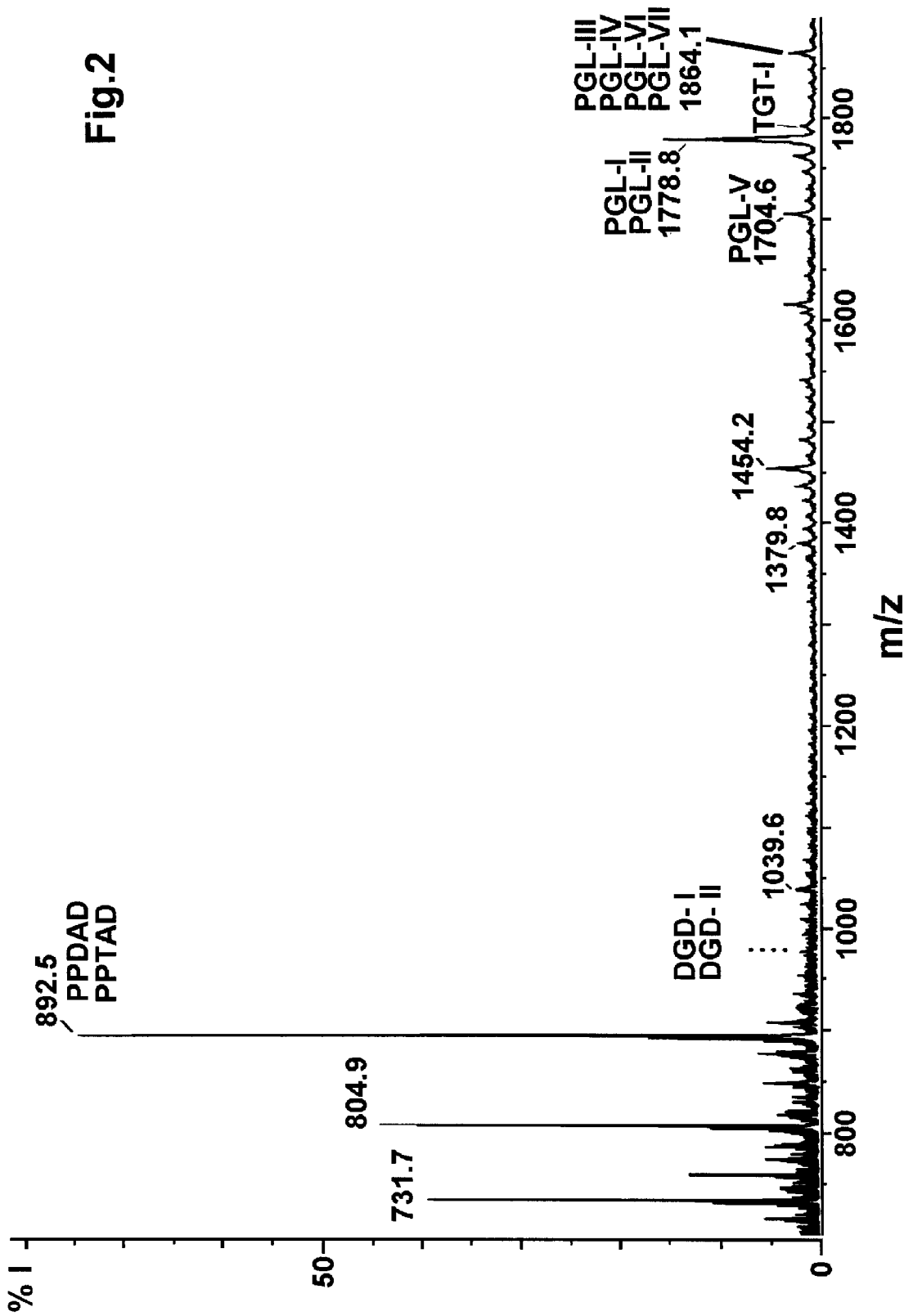
FIG. 2 is a negative FAB MS (fast atom bombardment mass spectrometry) of the total polar lipid extracts of M. hungatei.
Figure 3A:
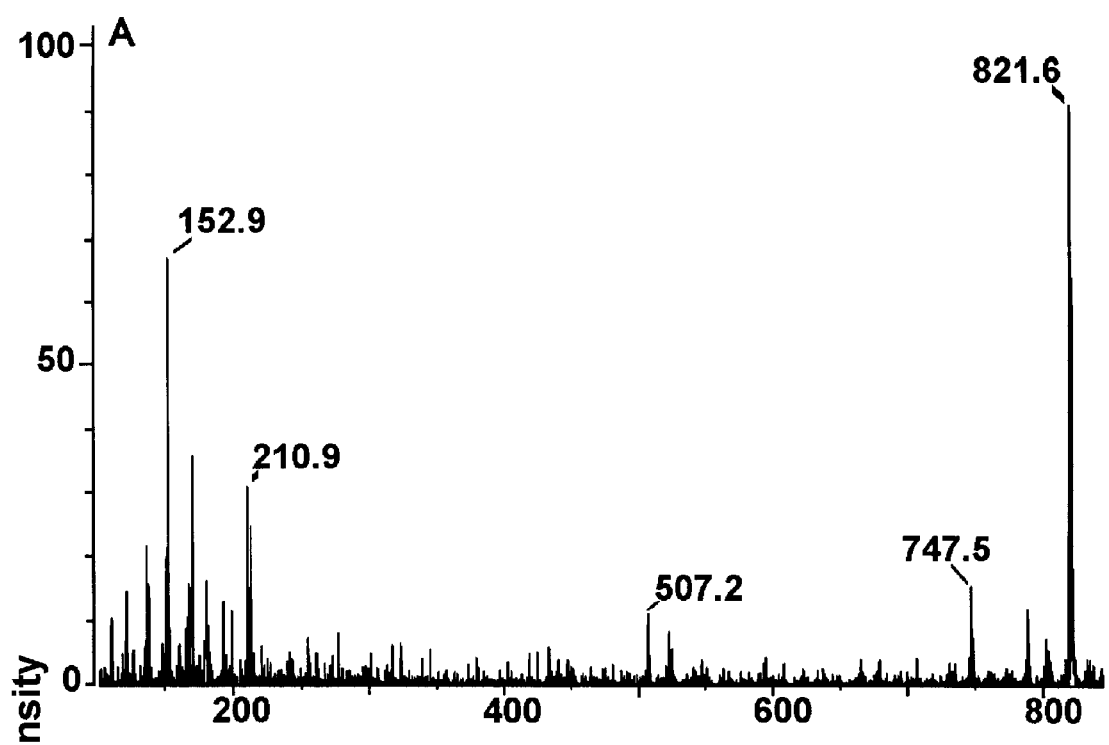
FIG. 3A and B represent the negative FAB MS spectra of novel, purified lipids from M. mazei. A=phosphatidylglycerol-hydroxydiether, and B=phosphatidylethanolamine-hydroxydiether.
Figure 3B:
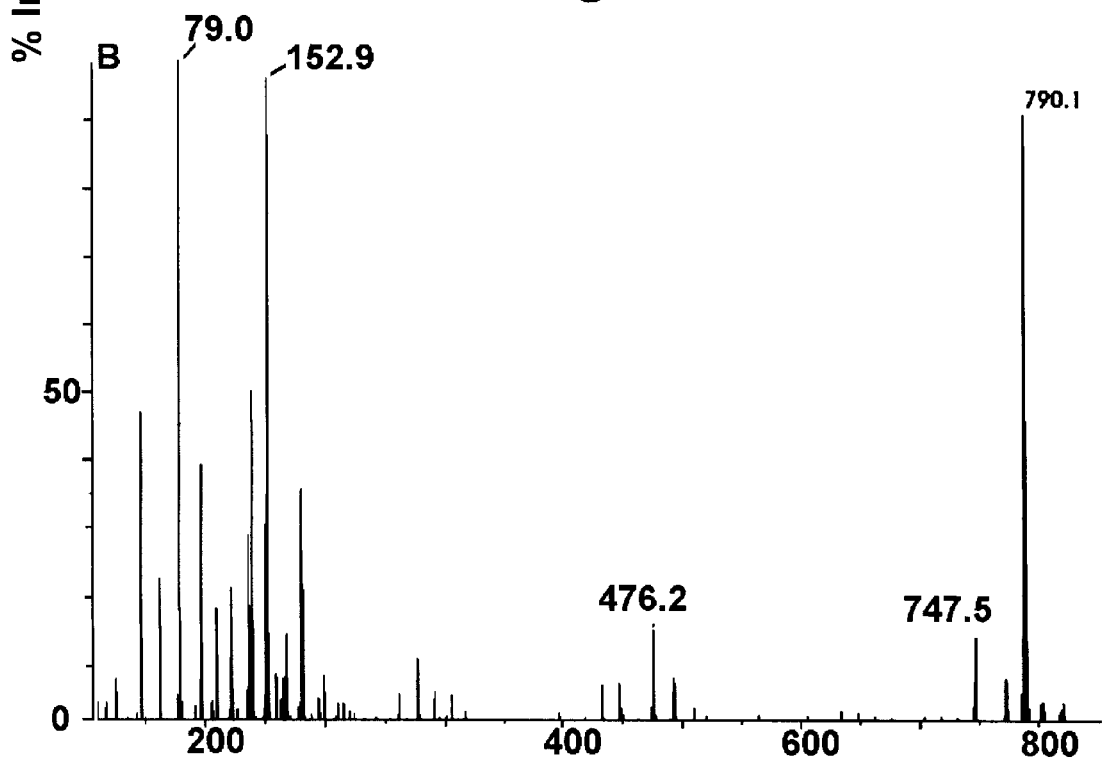

A negative FAB MS of the total polar lipids of *M. hungatei* revealed the phosphatidyldiether (731.7) and phosphatidyltetraether (1379.8) fragments (FIG. 2). Lipids lacking a phosphate moiety are detected with low sensitivity by this method, nevertheless signals corresponding to the structures of the purified lipids could be assigned. Calculated values agree with the structures and are PPDAD (M=892), PPTAD (M-15=892), DGD-I and DGD-II (M-1=975), PGL-V (M=1703), PGL-I and PGL-II (M=1778), TGT-I (M-1=1786), PGL-III and IV (M-15=1865) and PGL-VI and VII (M=1865). The large signal at 804.9 indicates a phosphatidylglyceroldiether (theoretical M=805) of the same structure as PG found in *Halobacterium cutirubrum* [Kates, M. (1978) Prog. Chem. Fats other Lipids 15: 301–342].

All $^{13}$C NMR signals of the phytanyl chains were in keeping with $C_{40,40}$-tetraether or $C_{20,20}$-diether lipids [Ekiel, I., et al. (1983) J. Bacteriol. 156: 316–326; Sprott, G. D., et al. (1990) J. Biol. Chem. 265: 13735–13740]. Further, lipid cores following head group removal had mobilities on TLC identical to the reference $C_{40,40}$-tetraether standards prepared from *M. hungatei* [Kushwaha, S. C., et al., (1981)] and $C_{20,20}$-diether from *Halobacterium cutirubrum* [Kates, M. (1978)].

Identification of the headgroup structures was one using two-dimensional homo- and heteronuclear NMR (COSY, RELAY COSY and HKQC=heteronuclear multiple quantum oherence experiments). Assigned $^{13}$C NMR signals are shown in Tables 4A and 4B for structures novel to this study and for those not fully characterized in previous studies [Kushwaha, S. C. et al. (1981) Biochim. Biophys. Acta 664: 156–173; and Ferrante, G. et al. (1988) Biochim. Biophys. Acta 963: 162–172]. $^{13}$NMR signals show that most of the lipids have a disaccharide (either α-glc$_p$-(1–2)-β-gal$_f$ or β-gal$_f$-(1–6)-β-gal$_f$) as one of the headgroups ($R_2$). The second headgroup ($R_1$) linked sn-1' in tetraethers is more diverse, either being a carbohydrate (β-gal$_f$, in TGT-I, phosphatidyl-N,N-dimethylaminopentanetetrol in PGL-V, PGL-VI, PGL-VII; the N,N,N-trimethyl in PGL-III, and PGL-IV; or glycerol in PGL-I). Some of the tetraethers have only one headgroup, which is clearly supported by characteristic $^{13}$C NMR chemical shifts of one of the sn-1 carbons of glycerol (Tables 4A and 4B).

TABLE 4A $^{13}C$ NMR chemical shifts for lipids[1] from *M. hungatei* in which $R_2$ is α-glc$_p$-(1–2)-β-gal$_t$

| Group | Carbon number | DGD-I | DGT-1 | PGL-1 | PGL-VI | PGL-111 | TGT-1 |
|---|---|---|---|---|---|---|---|
| $R_2$ | 1 | 107.20 | 107.17 | 107.17 | 107.19 | 107.26 | 107.16 |
| 1$^{st}$ moiety | 2 | 89.18 | 89.13 | 89.30 | 89.11 | 89.32 | 89.28 |
|  | 3 | 76.69 | 76.73 | 76.76 | 76.81 | 76.79 | 76.75 |
|  | 4 | 83.29 | 83.45 | 83.46 | 83.57 | 83.39 | 83.51 |
|  | 5 | 71.57 | 71.58 | 71.66* | 71.7* | 71.85* | 71.65 |
|  | 6 | 64.26 | 64.53 | 64.57 | 64.69 | 64.66 | 64.54 |
| $R_2$ | 1 | 99.67 | 99.64 | 99.71 | 99.70 | 99.79 | 99.71 |
| 2$^{nd}$moiety | 2 | 72.85 | 72.78 | 72.84 | 72.85 | 72.93 | 72.82 |
|  | 3 | 74.51 | 74.44 | 74.54 | 74.55 | 74.60 | 74.59 |
|  | 4 | 71.57 | 71.49 | 71.57* | 71.61* | 71.60* | 71.65 |
|  | 5 | 73.68 | 73.66 | 73.69 | 73.78 | 73.79 | 73.68 |
|  | 6 | 62.60 | 62.63 | 62.74 | 62.77 | 62.73 | 62.76 |
| $R_1$ | 1 | — | — | 63.04 | 60.48 | 67.83 | 109.13 |
|  | 2 | — | — | 70.93 | 72.05 | 72.35 | 81.55 |
|  | 3 | — | — | 68.55 | 73.20 | 73.52 | 78.96 |
|  | 4 | — | — | — | 72.85 | 73.22 | 85.86 |
|  | 5 | — | — | — | 64.37 | 64.66 | 72.11 |
|  | 6 | — | — | — | — | — | 64.25 |
|  | N—CH$_3$ | — | — | — | 42.42 | 54.33 | — |
|  | N—CH$_3$ | — | — | — | 44.85 | — | — |
| Glycerol | 1 | 67.88 | 67.71 | 67.79 | 67.83 | 67.87 | 67.79* |
|  | 2 | 78.61 | 78.53 | 78.58 | 78.63 | 78.68 | 78.57^ |
|  | 3 | 71.73 | 71.72 | 71.76 | 71.86 | 71.88 | 71.65 |
| Glycerol | 1 | — | 62.63 | 67.09 | 66.30 | 65.92 | 67.46* |
|  | 2 | — | 79.98 | 78.28 | 78.87 | 78.95 | 78.45^ |
|  | 3 | — | 71.72 | 71.66 | 71.61 | 71.49 | 71.65 |

*, ^ Assignments of these signals may be reversed.
[1]DGD, diglycosyldiether; DGT, diglycosyltetrather; PLG, phosphoglycolipid, TGT, triglycosyltetraether

TABLE 4B $^{13}C$ NMR chemical shifts for lipids from *M. hungatei* in which $R_2$ is β-gal$_f$-(1–6)-β-gal$_f$ or β-gal$_f$

| Group | Carbon number | DGD-II | DGT-II | PGL-IV | PGL-V | PGL-VII |
|---|---|---|---|---|---|---|
| $R_2$ | 1 | 109.16 | 109.12 | 109.25 | 109.01 | 109.22 |
| 1$^{st}$ moiety | 2 | 81.35 | 81.13* | 81.92 | 81.40 | 81.76 |
|  | 3 | 79.12 | 78.73 | 79.06 | 78.86 | 79.08 |
|  | 4 | 86.55 | 86.85 | 86.07 | 85.92 | 86.21 |
|  | 5 | 70.86 | 70.76 | 70.97 | 71.98 | 70.94 |
|  | 6 | 70.38 | 70.28 | 70.42 | 64.16 | 70.41 |
| $R_2$ | 1 | 109.60 | 109.62 | 109.68 | — | 109.66 |
| 2$^{nd}$ moiety | 2 | 81.35 | 81.40* | 81.92 | — | 81.76 |
|  | 3 | 79.12 | 79.22 | 79.06 | — | 79.08 |
|  | 4 | 85.79 | 86.07 | 85.51 | — | 85.59 |
|  | 5 | 72.00 | 71.95 | 72.12 | — | 72.09 |
|  | 6 | 63.95 | 63.92 | 64.03 | — | 64.03 |
| $R_1$ | 1 | — | — | 67.72 | 60.22 | 60.60 |
|  | 2 | — | — | 62.33 | 71.80 | 71.81 |
|  | 3 | — | — | 73.47 | 73.02 | 73.40 |
|  | 4 | — | — | 73.19 | 72.57 | 72.75 |
|  | 5 | — | — | 64.6 | 64.26 | 64.26 |
|  | N—CH$_3$ | — | — | 54.21 | 43.4(br) | 43.2(br) |
| glycerol | 1 | 67.53 | 67.38 | 67.72 | 67.29 | 67.67 |
|  | 2 | 78.38 | 78.32 | 78.55 | 78.32 | 78.50 |
|  | 3 | 71.46 | 71.59^ | 71.69^ | 71.37^ | 71.55 |
| glycerol | 1 | — | 62.77 | 65.87 | 66.12 | 66.19 |
|  | 2 | — | 79.8 | 78.90 | 78.63 | 78.80 |
|  | 3 | — | 71.69^ | 71.86^ | 71.54^ | 71.55 |

*, ^ Assignments of these signals may be reversed.
br, broad signal

Methanosarcina species. Lipids accounted for 3.8% of the cell dry weight of *M. mazei* and consisted of 90.2% polar lipids. Nine ether lipids were evident upon separation on thin-layer plates, plus 4 of lesser amounts of $R_f$<0.23, and several in trace quantities discovered by MS analysis. Purification was done for eight of the ether lipids collectively resenting 97–98% of the polar fraction. Each purified lipid had a major fragment at 747 or 731 indicating phosphatidyldiether lipids with or without a hydroxyl group on the phytanyl chain. Further characterization of lipid cores was done following hydrolysis of the total polar lipids and purification. These cores had optical rotation values of +37 and +55 and $^{13}C$ spectra with signals exactly as reported for the sn-2,3 configuration of hydroxydiether and standard diether $^{13}C$ NMR spectra with signals exactly as reported for the sn-2,3 configuration of hydroxydiether and standard diether lipids, respectively [Sprott, G. D., et al. (1990) J. Biol. Chem. 265: 13735–13740]. By reference to previous signal assignments, the NMR spectra further established conclusively that the hydroxyl group was in linkage to C-3 of the sn-2 phytanyl chain, as found for *M. barkeri* [Sprott, G. D. et al., (1990)].

Figure 4:
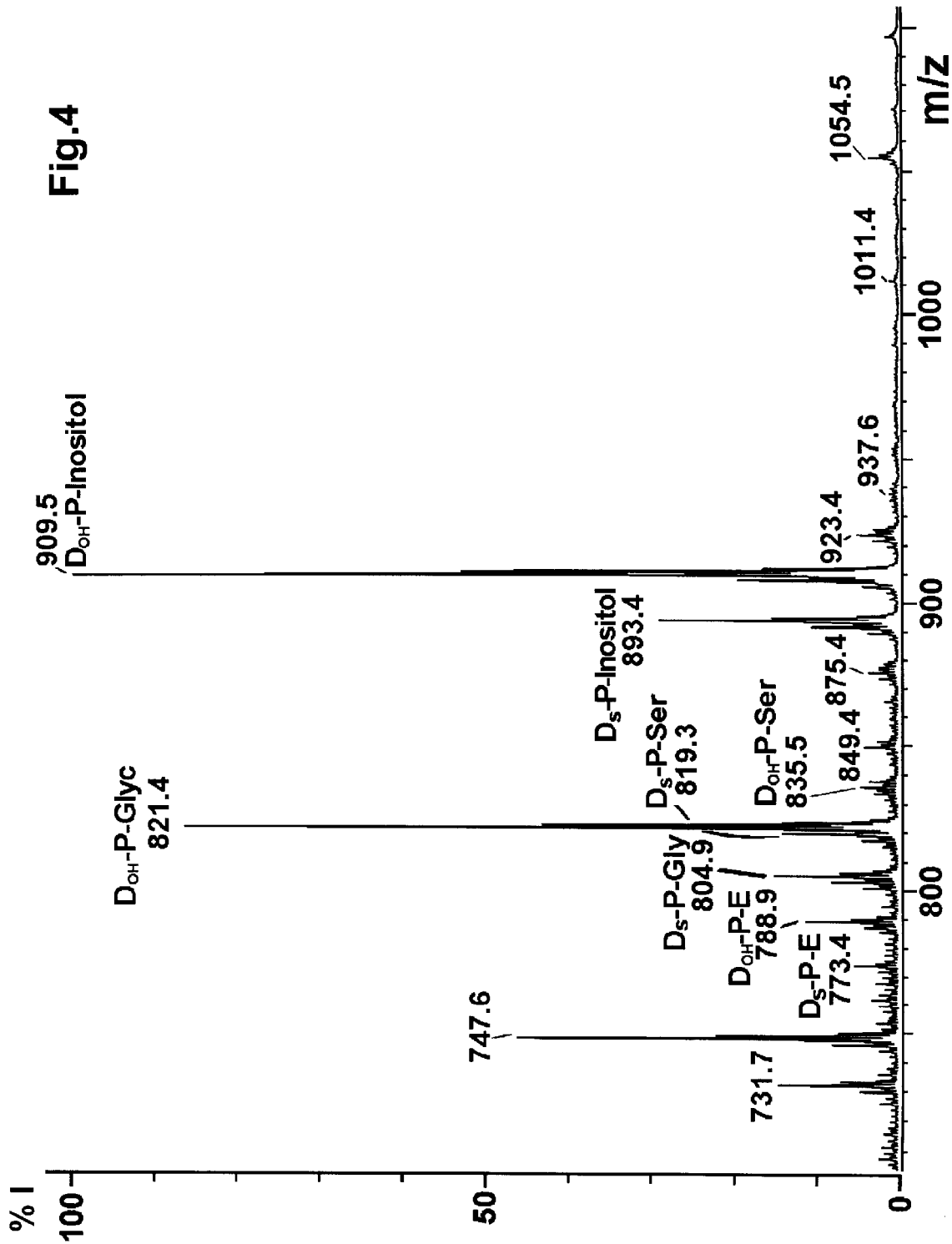
FIG. 4 is a similar spectrum for the total polar lipids from M. mazei.
Figure 5A:
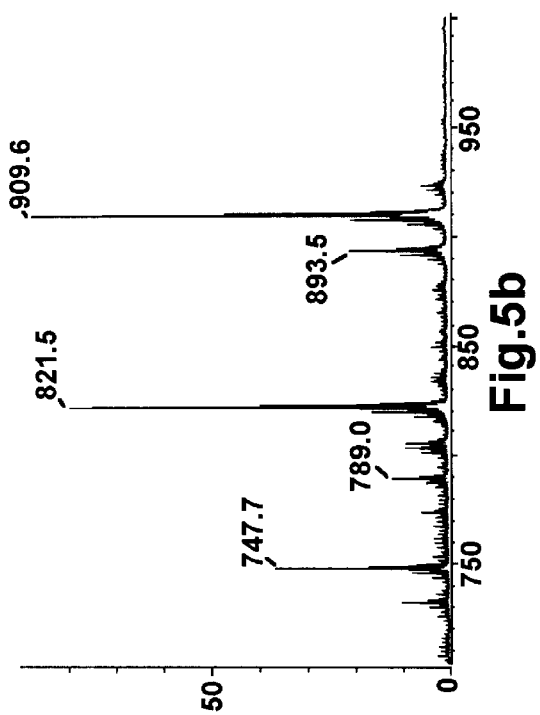
FIG. 5 is a comparison of the negative FAB MS of the total polar lipid extracts from various Methanosarcina spp. Specifically, A=M. thermophila (acetate grown), b=M. barkeri strain Fusaro (methanol grown), C=M. mazei (methanol grown), and D=M. acetivorans (methanol grown).
Figure 5B:
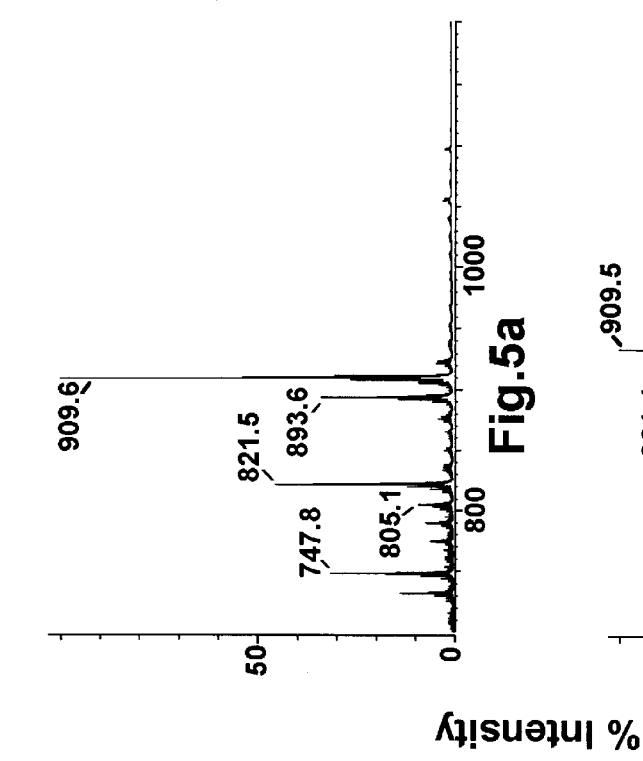
Figure 5C:
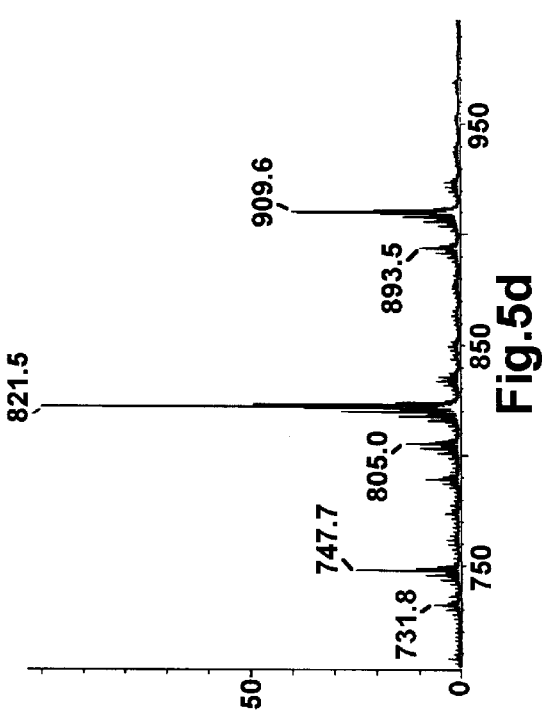
Figure 5D:
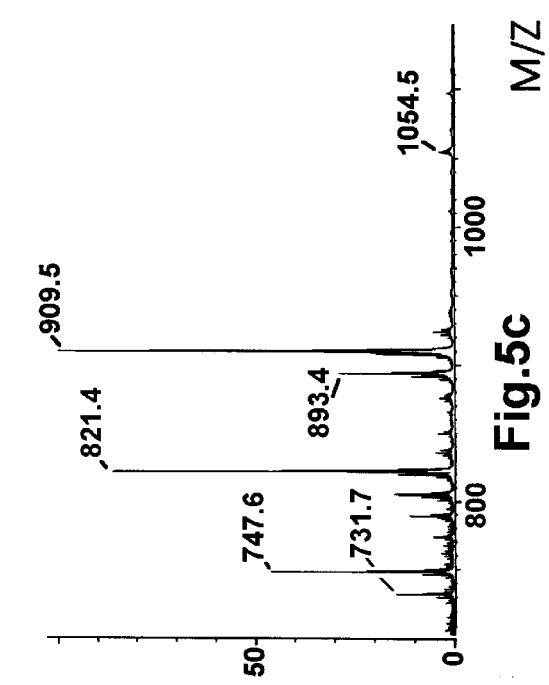

Negative and positive FAB MS analysis indicated the structures according to Formula III. Representative spectra are shown for purified phosphatidylglycerol-hydroxydiether and phosphatidylethanolamine-hydroxydiether (FIG. 4), and for the total polar lipids of *M. mazei* (FIG. 5). $^{13}C$ NMR spectra confirmed that the signals characteristic of inositol, serine, ethanolamine, and glycerol head groups were present. One purified lipid had a molecular weight of 804.9, supporting either a phosphatidylhydroxyglycine- or phosphatidylglycerol-diether.

Negative FAB MS of total polar lipid extracts allowed a comparison to be made with respect to the lipid components of other Methanosarcina species (FIG. 5). In all cases the same lipid molecular ions were present, although the ether lipids were present in the different species in different relative amounts.

Stability. Purification and storage of all ether lipids was conducted in an air atmosphere. No instabilities were found for any of the ether lipids during storage in air for periods of at least 1 year (longest period assayed).

LIPOSOMES PREPARED BY DETERGENT DIALYSIS

Mean sizes and size distributions. Controlled detergent dialysis was successfully used to form liposomes of good size homogeneity with total polar lipid extracts of 4 of the 5 methanogens tested (FIG. 6), the exception being *M. hungatei* liposomes (see below). Dynamic light scattering (DLS) analysis of the different liposome preparations yielded coefficients of variation of the size distribution between 0.2 and 0.5 (Table 5); the narrowest size distribution was obtained with *M. jannaschii* liposomes followed in decreasing order by those of *M. voltae, M. mazei* and *M. concilii*. DLS analysis was done in the vesicle-particle mode as number-weighted diameter distributions because the data agreed well with sizes and standard deviations calculated from microscopic examination (Table 5). Volume-weighted distributions always gave much larger diameter estimates (20 to 80%). The differences in homogeneity observed by DLS were confirmed by electron microscopy of negatively stained liposomes (FIG. 6 and Table 5). Importantly, the size distribution was very reproducible for different liposome preparations made from the same lipid extract (i.e. within 10%).

Large particles (>1 µm), easily observed with the light microscope, were present in the liposome suspension of *M. concilii* after dialysis. By electron microscopy, they appeared to be aggregates of various sized liposomes. Number-weighted DLS data revealed that removing these particles by filtration through a 0.22 µm nylon filter did not affect the mean diameter and size distribution of the population, as expected, because they only accounted for a very small fraction of the liposome population. In fact, in comparison with the smaller more numerous liposomes, they were judged to be few by electron microscopy. Once this small proportion of large vesicles was removed, a fairly homogeneous suspension of small liposomes remained (FIG. 6D).

The liposome population obtained with total polar lipids of *M. hungatei* was much more heterogeneous. Sizing of the liposomes by electron microscopy revealed the following distribution (FIG. 6E): 40% of the liposomes had diameters between 20 and 100 nm, 16% between 100 and 200 nm, 16% between 200 and 300 nm, and the remaining 28% between 300 and 1000 nm. Some of the electron microscopic fields did show good size distribution (FIG. 6F). Again, the large liposomes could be separated from the more uniform, smaller sized, liposomes by filtration.

The average size of the liposomes varied depending on the source of the lipids (Table 5). Unilamellar liposomes with mean diameters smaller than 100 nm were obtained with lipid extracts of *M. voltae, M. mazei, M. concilii* and *M. jannaschii* (grown at 50° C.) whereas larger (>100 nm) unilamellar liposomes were obtained with lipid extracts of *M. jannaschii* grown at 65° C.

The two extracts containing tetraether lipids, those from *M. jannaschii* grown at 65° C. and *M. hungatei*, yielded the larger liposomes. To determine whether the presence of tetraether lipids in the extracts could be responsible for these larger vesicles, liposomes were prepared from the total lipid extracts of *M. jannaschii* grown at 50° C. and at 65° C. Sprott et al. [sprott, G. D. et al. (1991) J. Bacteriol. 173: 3907–3910] have shown that *M. jannaschii* grown at 50° C. contains a higher proportion of diether lipids and less tetraether and macrocyclic diethers than cells grown at 65° C. (Table 1). As anticipated, the lipids obtained from *M. jannaschii* grown at 50° C. consistently yielded smaller liposomes than the liposomes obtained with lipids of *M. jannaschii* grown at 65° C. (Table 5).

TABLE 5

Size characteristics of liposomes prepared by detergent dialysis

| Origin of total polar lipid extract | Dynamic light scattering | | Electron microscopy | | Trapped volume (µl/mg lipid[2]) |
|---|---|---|---|---|---|
| | mean diameter (nm) | coefficient of variation[1] | mean diameter (nm) | coefficient of variation | |
| *M. jannaschii* | | | | | |
| (65° C.)[3] | 129 ± 31[4] | 0.24 | 113 ± 28[4] (282)[5] | 0.24 | 4.5 |
| (50° C.)[3] | 81 ± 22 | 0.27 | not determined | | 4.0 |
| *M. voltae* | 54 ± 19 | 0.35 | 56 ± 23 (298) | 0.41 | 4.5 |
| *M. mazei* | 45 ± 19 | 0.42 | 49 ± 21 (201) | 0.43 | 1.8 |
| *M. concilii*[6] | 69 ± 30 | 0.43 | 70 ± 38 (212) | 0.54 | 3.4 |

[1]coefficient of variation = standard deviation/mean diameter of the size distribution
[2]mg of total polar lipid
[3]growth temperature
[4]standard deviation
[5]number of liposomes measured
[6]liposomes were filtered through a 0.22 µm nylon filter to remove the large aggregates Intactness of archaecbacterial liposomes. In order to establish that the polar lipid extracts obtained from the different methanogens did indeed form closed intact vesicles, entrapment experiments with [$^{14}$C]sucrose were performed. From these experiments, the internal volumes of the different liposomes were obtained (Table 5). There is no absolute relationship between size and internal volume and this is probably due to the differences in lipid compositions of the extracts.

After a 2 week incubation period at 4° C., at least 92% of the marker was still present in the liposomes. Lysing the liposomes with 0.2% Triton X-100 released 100% of the label, while the incubation (4 hours) of empty liposomes with [$^{14}$C]sucrose (0.3 mCi/L) did not show an increase in radioactivity associated with the liposomes. These results confirmed that the [$^{14}$C]sucrose was entrapped and that the liposomes were sealed vesicles.

Figure 7:
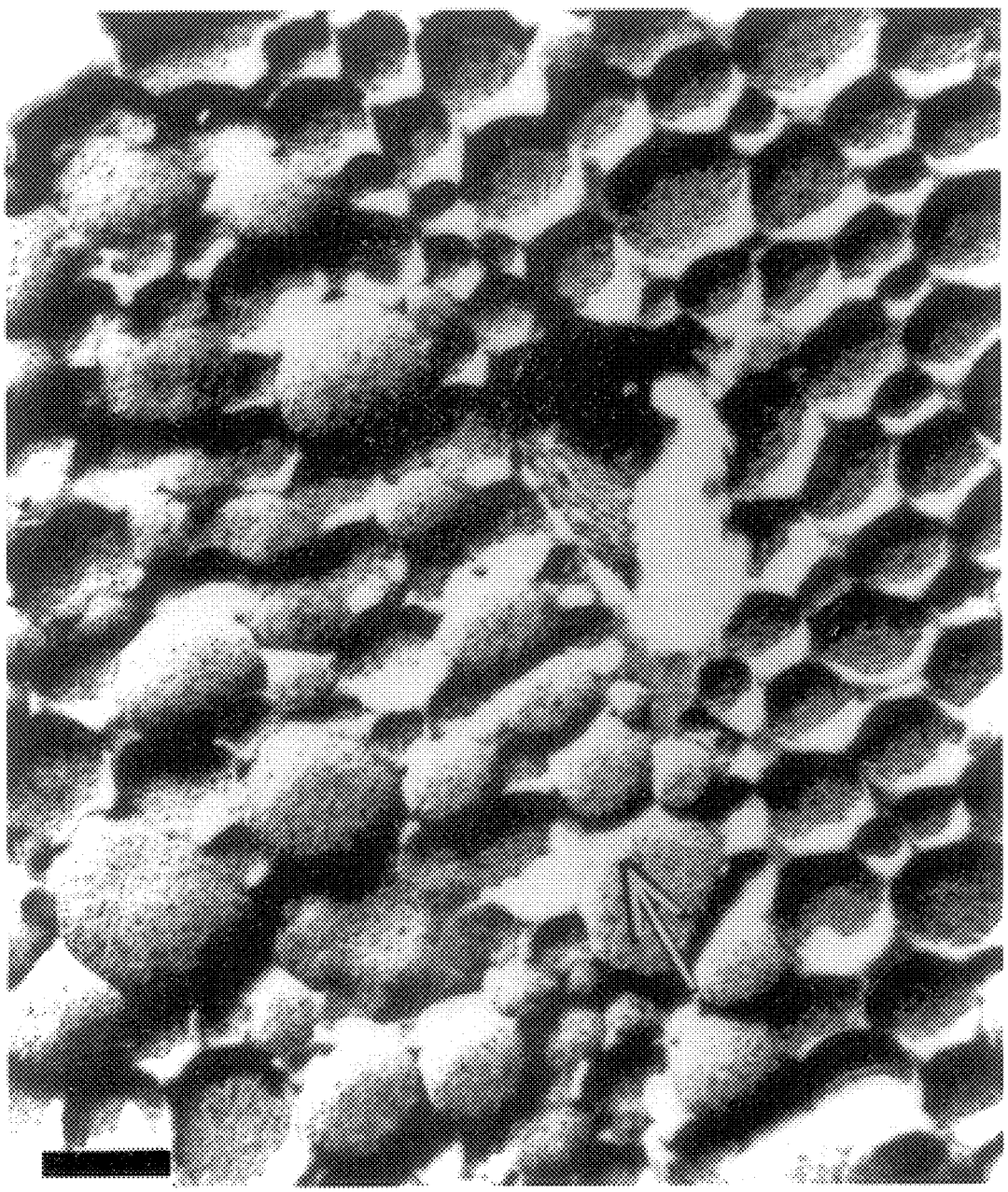
FIG. 7 is a TEM photograph of a freeze-fracture preparation of M. voltae liposomes. Bar=100 nm. The arrow denotes shadow direction.

Lamellarity of liposomes. Freeze-fractures of the liposomes from *M. jannaschii, M. voltae, M. mazei* and *M. concilii* (filtered) revealed them to be relatively homogeneous vesicles whose hydrophobic fracture surfaces (both concave and convex) were smooth (FIG. 7 is representative). Multiple fracture planes were never seen, which confirmed the unilamellar nature of these liposomes. Comparison of liposome diameters of freeze-fractures and negative stains showed that those from negative stains were slightly larger and suggested them to be somewhat flattened (and artificially expanded) as compared to the frozen preparations. A size correction factor of 0.71 was used, therefore, when calculating diameters of negatively stained liposomes [New, R.C.C. (1990.) In R.C.C. New (ed.) Liposomes. A Practical approach. IRL Press, Oxford]. *M. hungatei* liposomes were a mixture of unilamellar and numerous large. multilamellar vesicles.

Figure 8:
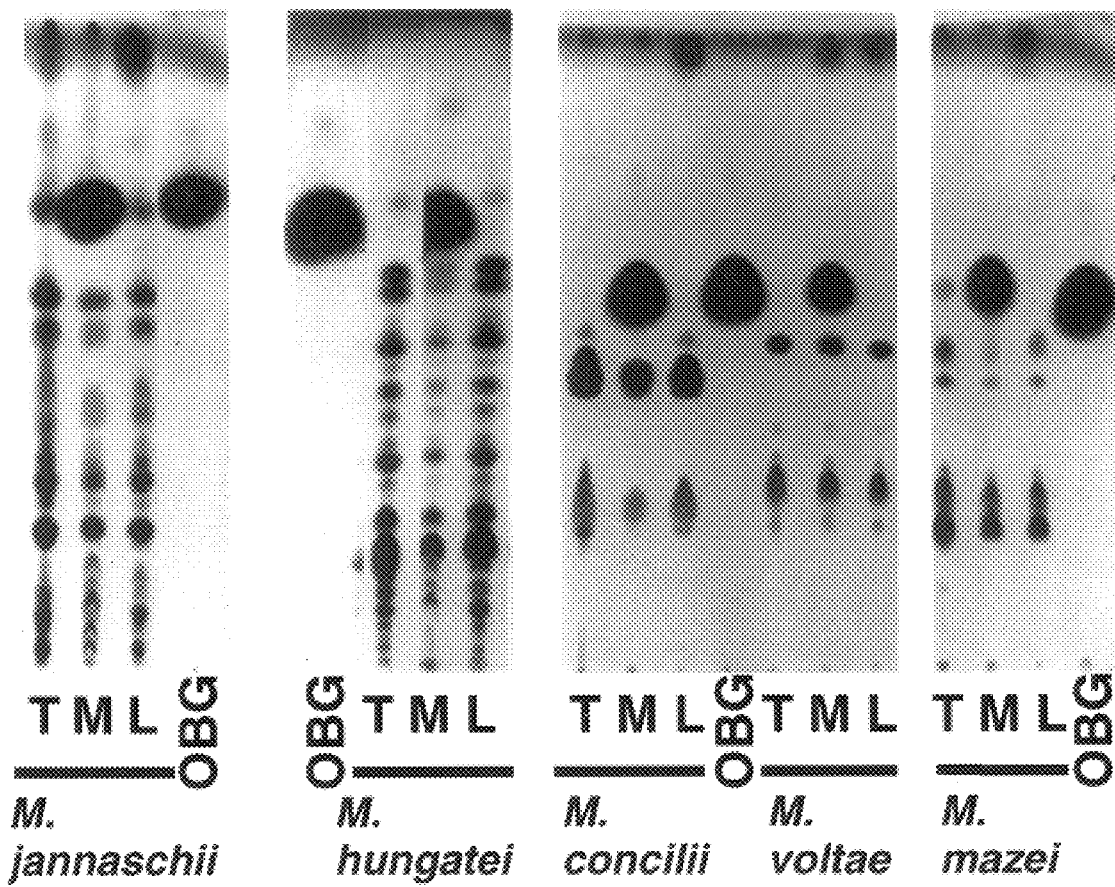
FIG. 8 illustrates the results of thin layer chromatography of total polar lipid extracts (T), mixed micelles (M) and liposomes (L), from various archaeobacteria, using the detergent octyl-β-D-glucopyranoside (OBG).

Lipid composition of liposomes. Comparison by thin layer chromatography among total polar lipid extracts, mixed micelles and liposomes revealed lipid profiles essentially identical (FIG. 8). This clearly indicates that all of the various ether lipid species were incorporated into each liposome preparation. Also note the different and characteristic lipid patterns of each methanogen. There was no residual detergent detected by thin layer chromatography in any of the liposome suspensions (FIG. 8) and, therefore, we estimate the detergent concentration to be less than 1 μg in the final liposome populations (40 mg lipid).

LIPOSOMES PREPARED BY LIPID EXTRUSION

Mean sizes and size distributions. Varisized ether liposomes were generated by pressure extrusion with 50, 100, 200 and 400 nm pore filters and different archaeobacterial lipid extracts (Table 6). With the smaller pore filters (50 and 100 nm pore size), most extracts yielded liposomes with mean diameters around 50 and 100 nm. However, with 200 nm pore filters only liposomes made from lipids of *M. smithii* and *M. hungatei* had mean diameters close to 200 nm, while liposomes obtained with polar lipids of *H. cutirubrum* in the presence of 4.0 M NaCl were considerably, larger than the pore of the filter; the remaining extracts yielded liposomes with mean diameters much smaller than 200 nm. With 400 nm port filters, only the liposomes generated from *H. cutirubrum* lipids (in 4.0 M NaCl) were larger than the pore size of the filter; the others were much smaller than the porosity of the filter.

Figure 9:
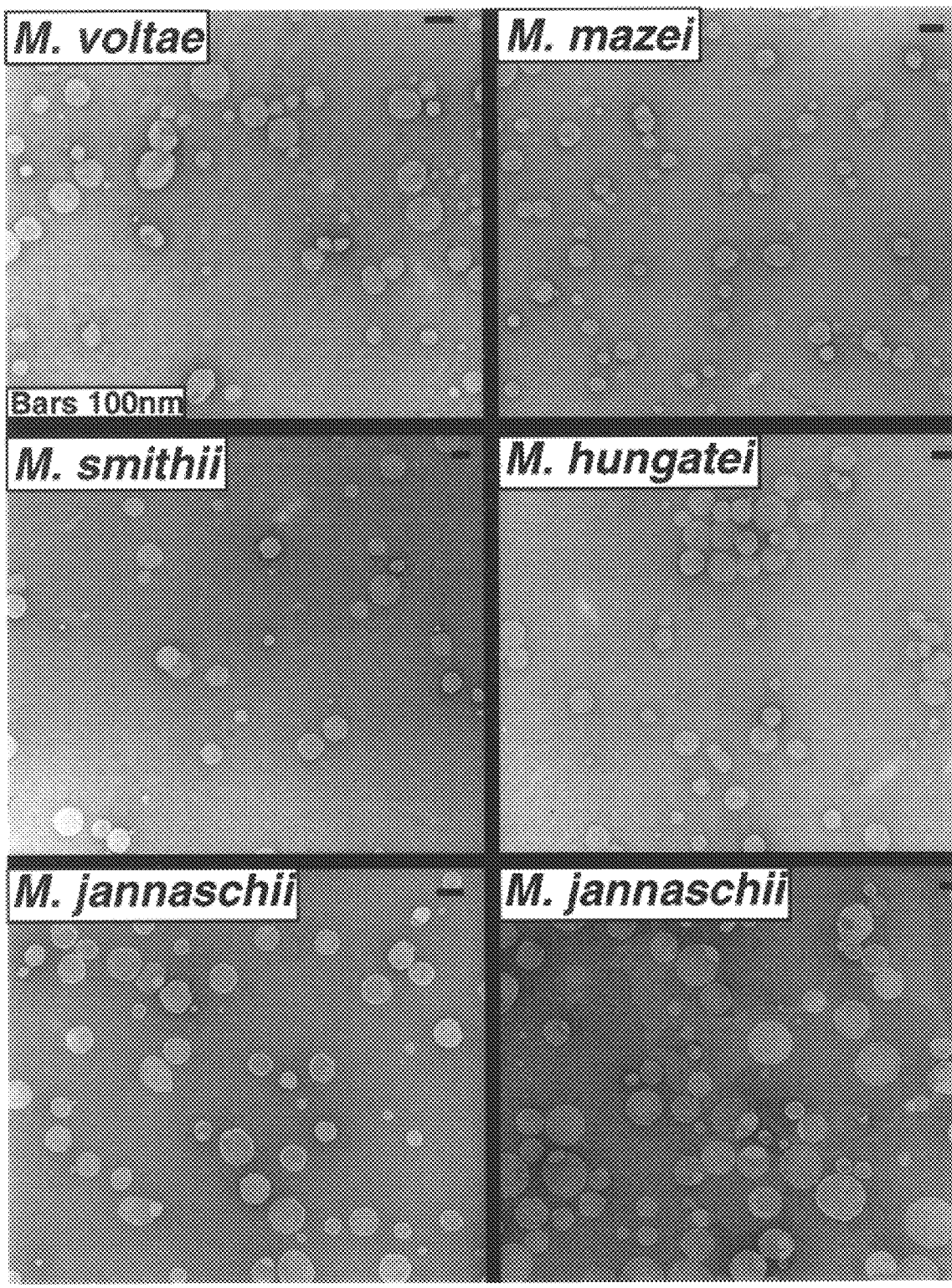
FIG. 9 is a series of TEM photographs of negatively stained liposomes obtained by pressure extrusion of the total polar lipid extracts from M. jannaschii, M. smithii, M. hungatei, M. mazei, and M. voltae through 100 nm pore size filters. Liposomes from M. jannaschii in right-hand panel are obtained by extrusion through a 200 nm filter.

The coefficient of correlations of the size distributions (between 0.20 and 0.40) obtained by dynamic light scattering analysis (DLS) revealed that all the liposome suspensions had good size homogeneity (Table 6). Electron micrographs of negatively-stained liposomes supported these findings (FIG. 9).

The pH of the extrusion buffer can have an effect on the mean diameter of the resulting liposomes (Table 7). of the representative extracts used in this study, those of *M. jannaschii* (grown at 65° C.) and *M. mazei* yielded larger liposomes with increasing acidic conditions. However, this effect was not evident with polar lipids of *M. jannaschii* grown at 50° C. Therefore, it must be dependent on the lipid composition of each extract.

TABLE 6

Size characteristics (mean diameter ± standard deviation of the mean) of the different lipsome suspensions prepared by pressure extrusion

| origin of total polar lipid extract | storage time at 4° C. (months) | 50 nm pore filter | 100 nm pore filter | 200 nm pore filter | 400 nm pore filter |
|---|---|---|---|---|---|
| METHANOGENS | | | | | |
| *M. jannaschii* | | | | | |
| grown at 65° C. | 0 | 69 ± 25 (0.36)[1] | 115 ± 26 (0.23) | 158 ± 53 (0.34) | 182 ± 71 (0.39) |
| | 4 | N.A.[2] | 112 ± 31 (0.28) | 158 ± 51 (0.33) | 193 ± 66 (0.34) |
| grown at 50° C. | 0 | 62 ± 15 (0.24) | 97 ± 23 (0.24) | 168 ± 52 (0.31) | 158 ± 61 (0.39) |
| *M. smithii* | 0 | 92 ± 24 (0.26) | 128 ± 37 (0.29) | 198 ± 54 (0.27) | 226 ± 71 (0.31) |
| | 4 | 114 ± 45 (0.39) | 154 ± 28 (0.18) | 191 ± 61 (0.32) | 200 ± 84 (0.42) |
| *M. hungatei* | 0 | 79 ± 20 (0.26) | 114 ± 27 (0.24) | 182 ± 46 (0.25) | 189 ± 63 (0.33) |
| | 4 | 73 ± 20 (0.27) | 114 ± 26 (0.23) | 183 ± 53 (0.29) | 225 ± 30 (0.13) |
| *M. voltae* | 0 | 67 ± 24 (0.36) | 93 ± 28 (0.30) | 141 ± 43 (0.30) | 174 ± 61 (0.35) |
| | 4 | 77 ± 22 (0.28) | 72 ± 23 (0.32) | 142 ± 19 (0.11) | 166 ± 21 (0.12) |
| *M. mazei* | 0 | 45 ± 15 (0.32) | 79 ± 23 (0.29) | 114 ± 44 (0.39) | 134 ± 54 (0.40) |
| *M. espanolae* | 0 | N.A. | 136 ± 36 (0.26) | N.A. | N.A. |
| EXTREME HALOPHILES | | | | | |
| *H. cutirubrum* | 0 | 60 ± 13 (0.21) | 78 ± 25 (0.32) | 139 ± 53 (0.38) | 160 ± 62 (0.38) |
| | 2 | 45 ± 16 (0.36) | 61 ± 25 (0.42) | 151 ± 51 (0.34) | 170 ± 59 (0.35) |
| *H. cutirubrum* (4.0M NaCl) | 0 | 84 ± 24 (0.29) | 113 ± 42 (0.37) | 315 ± 44 (0.14) | 456 ± 57 (0.13) |
| | 2 | N.A. | 124 ± 39 (0.32) | 273 ± 84 (0.31) | 393 ± 113 (0.29) |
| *N. magadii* | 0 | 46 ± 17 (0.36) | 69 ± 23 (0.34) | 85 ± 37 (0.43) | 93 ± 42 (0.45) |
| *N. magadii (4.0M NaCl)* | 0 | 60 ± 23 (0.38) | 102 ± 37 (0.37) | 151 ± 55 (0.36) | 179 ± 67 (0.38) |
| THERMOACIDOPHILES | | | | | |
| *T. acidophilum* | 0 | 82 ± 21 (0.26) | 136 ± 32 (0.24) | 183 ± 47 (0.26) | 197 ± 84 (0.43) |

[1]coefficient of variation of the size distribution = standard deviation/mean diameter
[2]data not available
[3]liposomes formed in extrusion buffer containing 4.0M NaCl

TABLE 7

Effect on pH on the mean diameter of unilamellar liposomes following pressure extrusion and storage

| origin of total polar lipid extract | storage time[2] (months) | mean diameters of liposomes populations formed and stored at different pH's | | | |
|---|---|---|---|---|---|
| | | 3.0 | 5.3 | 7.1 | 10.0 |
| M. jannaschii grown at 50° C. | 0 | 107 ± 28[3] (0.26[4]) | | 96 ± 23 (0.24) | 102 ± 23 (0.23) |
| | 2 | 101 ± 27 (0.26) | | 99 ± 26 (0.26) | 106 ± 26 (0.25) |
| | 5 | 111 ± 28 (0.25) | | 101 ± 22 (0.22) | 98 ± 23 (0.23) |
| | 8 | 107 ± 28 (0.26) | | 108 ± 21 (0.20) | 99 ± 30 (0.30) |
| M. jannaschii grown at 65° C. | 0 | 130 ± 27 (0.21) | | 115 ± 27 (0.23) | 97 ± 27 (0.28) |
| | 2 | 134 ± 45 (0.33) | | 113 ± 33 (0.29) | 95 ± 27 (0.28) |
| | 5 | 127 ± 45 (0.36) | | 112 ± 31 (0.28) | 100 ± 25 (0.25) |
| | 8 | 118 ± 46 (0.38) | | 110 ± 32 (0.29) | 101 ± 31 (0.31) |
| M. mazei | 0 | 92 ± 24 (0.26) | | 79 ± 23 (0.29) | 71 ± 22 (0.31) |
| | 2 | 99 ± 40 (0.40) | | 72 ± 24 (0.33) | 75 ± 20 (0.27) |
| | 5 | 88 ± 35 (0.35) | | 80 ± 22 (0.28) | N.A.[5] |
| | 8 | 81 ± 29 (0.36) | | 68 ± 26 (0.38) | 65 ± 15 (0.25) |
| M. hungatei | 0 | 108 ± 29 (0.27) | 129 ± 26 (0.26) | 117 ± 31 (0.26) | 132 ± 29 (0.22) |
| M. espanolae | 0 | 134 ± 37 (0.28) | 123 ± 23 (0.19) | 122 ± 30 (0.25) | 163 ± 26 (0.16) |
| M. magadii | 0 | 63 ± 18 (0.29) | 81 ± 22 (0.27) | 63 ± 10 (0.30) | 53 ± 24 (0.45) |
| T. acidophilum | 0 | 112 ± 27 (0.28) | 90 ± 31 (0.34) | 116 ± 32 (0.27) | 141 ± 34 (0.24) |

[1]liposomes were generated with 100 nm pore filters and stored at the pH's indicated
[2]liposomes were stored at room temperature
[3]standard deviation of the mean
[4]coefficient of variation of the size distribution
[5]data not available Lamellarity. The negatively-stained preparation also revealed that the liposomes formed with 50 and 100 nm pore filters were unilamellar (FIG. 9). However, numerous multilamellar liposomes were observed in suspensions generated with the larger 200 and 400 nm pore filters.

Stability studies

PHOSPHOLIPASES. With the exception of liposomes made from lipids of H. cutirubrum, all ether liposomes are stable in the presence of phospholipases A[2] and B (Table 8). In fact ether liposomes incubated in the presence of these enzymes retained entrapped dye equivalent to the "no phospholipase" controls. These results contrast to similar experiments conducted with liposomes made from the ester lipids DPPC and EPC. Following incubation with phospholipase NICOMP analysis failed to detect ester liposomes, because of lost structural integrity.

Ether liposomes were, however, susceptible to hydrolysis with phospholipase C. Nevertheless, some were more resistant than ester liposomes, namely those of M. hungatei, M. smithii and M. jannaschii (grown at 65° C.).

TABLE 8

Effects of phospholipases on ester and ether liposomes[1]

| | phospholipase A[2] | | phospholipase B | | phospholipase C | |
|---|---|---|---|---|---|---|
| source of lipid extract | Time[2] (h) | % CF leakage | Time (h) | % CF leakage | Time (min) | % CF leakage |
| ESTER LIPOSOMES | | | | | | |
| EPC | 1 | 100 (10[3]) | 4 | 60 (18) | 5 | 100 (0) |
| DPPC | 4 | 75 (4) | 4 | 91 (6) | 15 | 88 (2) |
| ETHER LIPOSOMES | | | | | | |
| H. cutirubrum | 1 | 70 (0) | 1 | 88 (0) | 5 | 100 (8) |
| M. mazei | 4 | 18 (13) | 4 | 6 (4) | 5 | 100 (7) |
| M. voltae | 4 | 15 (0) | 4 | 2 (0) | 15 | 85 (2) |
| M. smithii | 4 | 23 (10) | 4 | 0 (0) | 60 | 75 (3) |
| M. jannaschii | | | | | | |
| grown at 50° C. | 4 | 9 (6) | 4 | 5 (3) | 15 | 75 (0) |
| grown at 65° C. | 4 | 7 (7) | 4 | 5 (3) | 60 | 30 (1) |
| M. hungatei | 4 | 4 (2) | 4 | 4 (2) | 60 | 60 (0) |

[1]Results are expressed as % leakage of carboxyfluorescein.
[2]Time of incubation in the presence of the enzyme.
[3]Controls expressed as % leakage of carboxyfluorescein from liposomes in the absence of enzyme.

TEMPERATURE. Extracts of ether lipids yielded more stable liposomes at the higher temperatures than the ester lipids DPPC and EPC (Table 9); the leakage of 5(6)-carboxyfluorescein at 50 and 65° C. was less severe with the ether liposomes. At temperatures below 50° C., the dye was released from ether liposomes and DPPC liposomes at similar rates. In general, EP liposomes were more leaky than those from DPPC or from ether liposomes prepared from the total polar lipids of M. jannaschii.

Of the ether liposomes, those generated with lipids of M. hungatei and M. jannaschii were the most stable. This is likely due to the presence of tetraether lipids in those extracts; M. mazei has no tetraether lipids. Sprott et al. (1991) have shown that M. jannaschii grown at 50° C. contains higher proportions of standard diether lipids and less tetraether and macrocyclic diethers than cells grown at 65° C. Therefore, the stability of liposomes made from lipids of cells grown at both temperatures were tested at 35, 50 and 65° C. The liposomes containing less tetraethers were consistently more leaky than those prepared from lipids of cells grown at 65° C. (Table 10). This finding was further supported by leakage studies done with liposomes of varying amounts of tetraether lipids made with total polar lipids of M. voltae and M. hungatei (Table 10), i.e. the liposomes containing more tetraethers were consistently less leaky.

Removal of microbial and viral contaminants without loss of structural properties and/or of the encapsulated compound is desirable in pharmaceutical applications of liposomes. Filter sterilization suffers from the problems of not removing viral particles or pyrogens, and being unsuitable for large liposomes of 500 nm or more [Friese, J. (1984) Chapter 10, In Liposome technology, Vol. 1. Preparation of liposomes. G. Gregoriadus (ed.) CRC Press]. A convenient alternative method which avoids these problems is autoclaving, but this method is not possible with ester lipid derived liposomes because the structural integrity of the liposomes is lost during the heat treatment [Friese, J. (1984)].

Autoclave treatment was tested on archaeobacterial ether liposomes suspended in the buffer-NaCl system used during their construction. See table II. None of the ether liposomes showed signs of fusion (mean diameter) or lysis (intensity). The fluorescent dye was retained to differing extents during autoclaving in the different liposome preparations, exhibiting a direct correlation between retention and tetraether content. This is a major advantage of the novel ether liposomes according to the invention.

TABLE 9

Effect of temperature on leakiness of carboxyfluorescein from liposomes[1]

| Incubation temperature (° C.) | Incubation time (days) | EPC | DPPC | M. hungatei | M. jannaschii[2] | M. mazei |
|---|---|---|---|---|---|---|
| 4 | 1 | 11 | 1 | 0 | 0 | 0 |
|   | 7 | 31 | 2 | 1 | 3 | 5 |
|   | 45 |   | 9 | 5 | 4 | 28 |
| 25 | 1 | 24 | 1 | 1 | 6 | 6 |
|   | 7 | 58 | 6 | 1 | 9 | 52 |
|   | 45 | 100 | 22 | 12 | 24 | 94 |
| 35 | 1 | 49 | 4 | 1 | 3 | 29 |
|   | 7 | 78 | 7 | 1 | 16 | 76 |
| 50 | 1 | 83 | 100 | 3 | 11 | 56 |
|   | 3 | 82 |   | — | 14 | 62 |
|   | 7 | 90 |   | 16 | 24 | 76 |
| 65 | 1 | 100 | 100 | 12 | 17 | 74 |
|   | 3 |   |   | 32 | 20 | 100 |
|   | 7 |   |   | 58 | 44 |   |

[1]Results are expressed as % leakage of carboxyfluorescein.
[2]M. jannaschii grown at 65° C.

TABLE 10

Effects of increasing amounts of tetraether lipids on temperature stability of ether liposomes[1]

| source of lipids | % tetratethers in extract | Temperature in incubation 55° C. | 65° C. |
|---|---|---|---|
| M. jannaschii |   |   |   |
| grown at 50° C. | 21 | 27 | 40 |
| grown at 65° C. | 42 | 16 | 30 |
| M. voltae | 0 | 75 | 100 |
| M. voltae/M. hungatei[2] | 11 | 47 | 84 |
|   | 22 | 40 | 79 |
|   | 39 | 18 | 55 |
| M. hungatei | 50 | 12 | 25 |

[1]Results are expressed as % leakage of 5(6)-carboxyfluorescein after 6 day incubations.
[2]liposomes made of total polar lipids (TPL) of M. hungatei and M. voltae mixed in different proportions in order to vary the percent tetraether lipids of the liposomes.

TABLE 11

Effects of autoclaving (20 min., 121° C., 15 lb/in²) on archaeal liposomes

| source of lipids | % tetraether in extract | % leakage of CF[1] | Intemmity[1] before | Intemmity[1] after | mean diameter (nm ± standard deviation) before | mean diameter (nm ± standard deviation) after |
|---|---|---|---|---|---|---|
| *M. jannaschii* | | | | | | |
| grown at 50° C. | 21 | 15 | 465 | 450 | 85 ± 32 (0.38[3]) | 85 ± 31 (0.36) |
| grown at 65° C. | 42 | 11 | 450 | 490 | 128 ± 26 (0.21) | 123 ± 36 (0.29) |
| *M. mazei* | 0 | 51 | 425 | 424 | 81 ± 31 (0.38) | 91 ± 30 (0.33) |
| *M. smithii* | +[4] | 41 | 260 | 245 | 158 ± 48 (0.31) | 150 ± 61 (0.40) |
| *H. cutirubrum* | 0 | 66 | 145 | 175 | 72 ± 28 (0.38) | 76 ± 24 (0.32) |
| *M. voltae* | 0 | 28 | 365 | 334 | 70 ± 32 (0.45) | 74 ± 35 (0.47) |
| *M. voltae/M. hungatei*[3] | 11 | 10 | 450 | 400 | 104 ± 34 (0.33) | 111 ± 33 (0.30) |
| | 22 | 11 | 370 | 388 | 102 ± 34 (0.34) | 101 ± 35 (0.35) |
| | 39 | 9 | 450 | 400 | 114 ± 35 (0.31) | 105 ± 34 (0.32) |
| *M. hungatei* | 50 | 6 | 455 | 432 | 120 ± 37 (0.31) | 116 ± 37 (0.31) |

[1]measured with a Nicomp 370 submicron particle sizer at a sensitivity of 250 and a window width of 10 μsec.
[2]5(6)-carboxyfluorescein
[3]coefficient of variation of the size distribution = standard deviation/measured diameter
[4]contains tetraethers but the amount has not yet been determined
[5]liposomes made of TPL of *M. hungatei* and M. voltae mixed in different proportions in order to vary the percent tetraether lipids of the liposomes LEAKAGE OF [$^{14}$C] SUCROSE. The leakage of [$^{14}$C] sucrose during storage at 4° C. was studied (Table 12). At pH values 3.0 and 7.1, ether liposomes retained the solute as efficiently as ester liposomes (DPPC and EPC) and at pH 10.7, ether liposomes were much more efficient than EPC liposomes. The reason for the increase in entrapped [$^{14}$C] sucrose observed with DPPC liposomes at pH 10.7 is still unknown.

TABLE 12

Remaining entrapped [$^{14}$C]sucrose (%) after storage of unilamellar liposome suspensions at different pH's

| pH of liposome suspension[1] | storage time (days) | DPPC | EPC | Origin of total polar lipid extract *M. jannaschii*[2] | Origin of total polar lipid extract *M. jannaschii*[3] | Origin of total polar lipid extract *M. mazei* |
|---|---|---|---|---|---|---|
| 3.0 | 1 | 76 | 78 | 75 | 72 | 98 |
| | 28 | 78 | 53 | 77 | 71 | 80 |
| 7.1 | 1 | 95 | 100 | 91 | 94 | 86 |
| | 26 | 98 | 98 | 94 | 98 | 64 |
| 10.7 | 2 | 112 | 78 | 89 | 89 | 83 |
| | 20 | 133 | 2 | 90 | 94 | 75 |

[1]liposomes were generated with 100 nm pore filters and stored at 4° C. at the pH's indicated. 0.2% sodium azide was added to prevent bacterial growth.
[2]*M. jannaschii* grown at 50° C.
[3]*M. jannaschii* grown at 65° C.

VESICLE SIZE. DLS analysis was used to detect physical instability (fusion or aggregation) of unilamellar ether liposomes during long storage periods. After 2–5 months of incubation at 4° C., the mean diameter of most ether liposome populations had not changed significantly (Tables 6 and 7). In most cases the coefficients of variation of the size distributions were also unaffected, although a significant increase was observed at pH 3.0 with liposomes generated with lipids of *M. jannaschii* (65° C.) and *M. mazei*. This could be indicative of a shift in the liposome population.

DISCUSSION

Pure methanogenic ether lipids are not available commercially. Isolation of even the most predominant ones in quantity sufficient to attempt liposome formation is a monumental task, considering that most methanogens synthesize at least 10 different polar lipids (some such as *M. jannaschii* have many more). Also, the lipid fraction of most methanogen cells accounts for only about 5% of the cell dry weight. Therefore, we herein explored the feasibility of using natural mixtures of total polar lipids from different methanogens and other archaeobacteria to prepare ether liposome formulations.

We have successfully generated closed unilamellar vesicles with good size homogeneity from total polar lipid extracts of *M. voltae, M. jannaschii, M. mazei* and *M. concilii*. In comparison, coefficients of variation for the size distribution of liposomes obtained with archaeobacterial ether lipids and ester lipid (EPC) are comparable, using n-alkyl-glucoside as detergent [Mimms, L. T., et al. (1981) Biochemistry 20: 833–840; Schwendener, R. A., et al (1981) Biochim. Biophys. Res. Comm. 100: 1055–1062].

There is no strong correlation between the nature of the different core lipid structures in each extract and the size of the liposomes formed. However, the presence of tetraether core lipids does appear to promote the formation of larger vesicles. These observations are in agreement with the findings of Lelkes et al. [Lelkes, P. I., et al. (1983) Biochim. Biophys. Acta 732:714–718] who have shown that vesicles of egg phosphatidylcholine increased in size with increasing amounts of tetraethers incorporated. The packing constraints imposed on the rigid, membrane-spanning tetraether lipids (Lelkes, P. I., et al. (1983); Ring, K. et al. (1986)] are probably responsible for the observations mentioned above. These constraints would diminish with increasingly larger liposomes as the curvature of the liposome decreased. The differences in size could also be partly due to the differences in polar head group compositions of each lipid extract. It is well established that the nature of the head group partly determines the molecular structure/shape (inverted cone, cylindrical or cone) of the lipid component, which in turn determines its lipid packing order [Lichtenberg, D., and Barenholz, Y. (1988) Methods Biochem. Anal. 33:337–462. The intravesicular aqueous compartment can also be affected by the head group composition due to its hydration and bulkiness [Racey, T. J., et al. (1989) Chem. Phys. Lipids 49: 271–28].

Pressure extrusion has advantages relative to detergent dialysis, as applied to the preparation of archaeobacterial ether liposomes. Pressure extrusion is very rapid and simple, requiring only hand-homogenization of the dried lipid to disperse it into the aqueous buffer solution and extrusion of this dispersion several times through a filter. Inclusion in the buffer solution of a substance ($^{14}$C-sucrose and a fluorescent dye indicated the principle) resulted in its effective entrapment. Detergent dialysis, on the other hand, can result in poor entrapment if the substance being loaded is lost by dialysis. We used low volumes of about 1 ml for pressure extrusion, but the principle is the same and the equipment is readily available to allow scale-up (Avestin, Inc., Ottawa, Canada). This method avoids the use of detergent which may not be acceptable for pharmaceutical applications. Also, the size of the liposomes can readily be altered in a defined manner by simply changing the membrane pore size, whereas experimentation is required to alter conditions carefully to obtain a desired change in size by detergent dialysis [Zumbuehl, O., and Weder, H. G. (1981) Biochim Biophys Acta 640: 252–262; Schwendener, R. A., et al. (1981) Biochem. Biophys. Res. Com. 100:, 105571062; Aurora, T. S., et al. (1985) Biochim. Biophys Acta. 820: 250–258]. Finally, detergent dialysis of total ether lipids from *M. hungatei* produced a mixed population of liposomes consisting of small unilamellar and large multilamellar types ranging in size from 100 to 1000 nm. Pressure extrusion of these same preparations, which consist of diether and tetraether lipids in a ratio of about 1:1, yielded a highly homogeneous population. The size of these liposomes was in proportion to the pore size of the filter, as for other sources of lipid.

The ether lipids of *M. hungatei* have been partially characterized previously by Kushwaha et al. [Kushwaha, S. C., et al. (1981) Biochim. Biophys. Acta 664: 156–173] and Ferrante et al. [Ferrante, G. et al. (1987) Biochim. Biophys. Acta 921:.281–291]. New structures are presented for tetraether phosphoglycolipids PGL-III to VII, and a tetraether glycolipid TGT-I. On the basis of dry weight 16 lipids account for >99% of the ether lipids extracted from this methanogen.

*Methanosarcina barkeri* and *M. mazei* synthesize 3-hydroxydiether as well as standard diether lipids [Sprott, G. D., et al (1990) J. Biol. Chem. 265: 13735–13740. Although hydroxydietherphosphatidylserine and hydroxydiether phosphatidyl-myo-inositol have been found in *M. barkeri* [Nishihara, M. and Koga, Y. (1991) Biochim. Biophys Acta 1082: 211–217] and polar lipids of the Methanosarcina genera are otherwise uncharacterized. Here we present evidence for two novel hydroxydiether lipids having head groups of phosphoethanolamine and phosphoglycerol. Structural data are provided for 96 wt. % of the ether lipids of *M. mazei*. Negative FAB mass spectrometry provided comparative data on the polar lipids of various Methanosarcina species grown on various carbon sources, revealing that the same lipid molecular ions are present in all cases.

The ether lipid structures for both neutrophile and alkalophile groupings of the extreme halophiles has been determined in detail, as reviewed by M. Kates [in Handbook of lipid research (1990), pp. 1–122 (Kates, M., ed.), Plenum Press, New York and London]. Similarly reviewed are our structural data on the lipids of *Methanococcus voltae*, *Methanococcus jannaschii*, and *Methanosaeta concilii* [Sprott, G. D. (1992) T. Bioenergetics and Biomembranes 24: 555–566).

Phytanyl chains of archaeobacterial lipids are linked to the glycerol carbons by ether linkages. As opposed to the ester bonds which link fatty acyl chains to the glycerol carbons in eucaryotic and eubacterial membrane lipids, these bonds are not susceptible to enzymatic attack by phospholipases $A_2$ and B [DeBose, C. D. and Roberts, M. F. (1983) J. Biol. Chem. 258: 6327–6334]. In addition, phosphate ester bonds of ether phospholipids, unlike is similar bonds in ester phospholipids, are often resistant to enzymatic attack by phospholipase-C [Morii, H., et al. (1988) Agric. Biol. Chem. 52: 3149–3156; Morii, H. et al., (1986) J. Lipid Res. 27: 724–730; Burns, R. A., et al. (1981) Biochemistry 20: 5943–59503]. We have demonstrated that archaeobacterial ether lipids form liposomes that resist enzymatic attack (Table 8). The loss of structural integrity observed with ester liposomes (DPPC and EPC during incubation with phospholipases is in agreement with earlier reports [Davies, D. E., et al. (1991) Biochim. Biophys. Acta 1084: 29–34; Fugman, D. A., et al. (1984) Biochim. Biophys. Acta 795: 191–195; Rowland, R. N. and Woodley, J. F. (1980) Biochim. Biophys. Acta 620: 400–409].

In addition to enzymatic hydrolysis, ester bonds are also susceptible to chemical hydrolysis. In general, this process is accentuated at extreme pH's and with increasing temperatures [Frokjaer, S., et al. (1982) in Optimizatioan of drug delivery (Bundgaard, H., Bagger-Hansen, A. and Kofod, H., eds) Alfred Benzon Symp. 17, Munsgaard, Copenhagen, p. 384]. Hydrolysis may introduce free fatty acids and lysophospholipids into ester liposomes, two compounds that affect membrane integrity and dvnamics (Van Echteld et al., (1981). However, ether bonds are relatively resistant to chemical hydrolysis [Kates, M. (1986) in Laboratory Techniques in Biochemistry and Molecular biology (Burdon, R. H., and van Knippenberg, P. H., eds.), Vol. III, part II, Elsevier, New York, pp.123–127]. This characteristic may be partly responsible for the enhanced stability of ether liposomes at high temperatures (Tables 9, 10, 11) and extreme pH values (Table 12).

The presence of tetraether lipids is also a stabilizing factor of liposomes incubated at high temperatures (Table II). Ring et al (1986) have also shown that CF-loaded multilamellar liposomes generated from the main lipid component of *Thermoplasma acidophilum*, which is a tetraether monoglycosyl-phosphoryl glycerol lipid, are considerably less leaky than EPC or DPPC vesicles at high temperatures. Therefore, liposomes (uni- or multilamellar) made from archaeobacterial polar lipid extracts containing high amounts of tetraethers should be more stable at higher temperature than those made from extracts lacking tetraethers.

It is well documented that one of the major problems associated with ester liposomes is their oxidative degradation [Konings, A. W. T. (1984) in Liposome technology (G. Gregoriadis ,ed.) Vol. 1, CRC Press, Inc., Boca Raton, Fla., pp. 139–162]. Lipid peroxidation occurs because of the presence of unsaturated fatty acyl chains, as in egg phosphatidylcholine and, as a result of these changes, liposomes maintained in aqueous suspension may aggregate, fuse or leak their content (Lichtenberg, D., and Barenholz, Y. (1988) Methods Biochem. Anal. 33:337–462.; Goldstein, I. M. and Weissmann, (1987) Biochem. Biophys, Res. Comm. 75: 604–609]. Therefore, the use of archaeobacterial lipids would also minimize this problem, since the phytanyl chains are fully saturated.

Ether liposomes did not fuse or aggregate during storage at 4° C. over a period of 4 months (Table 6). It is important to note that the different polar ether lipid formulations yielded liposomes stable at all pH's studied. In ester liposomes, cholesterol is often required to increase stability and prevent their fusion or aggregation [Lichtenberg, D. and Barenholz, Y. (1988) Methods Biochem. Anal. 33:337–462].

The novel natural combination of lipids found in the total polar lipids extracted from each archaeobacterium provides, with no purification of individual lipid species being required, a suitable mix of ether lipids to prepare liposomes for stability studies. The source of these lipid mixes is important to the final liposome product obtained. For example, size varies with lipid formulation as well as with the membrane pore size (Table 6). Also, resistance to is elevated temperatures increased with increasing proportions of tetraether lipids (Table 10), indicating applications for liposomes made from the lipids of other archaeobacteria including Thermoplasma spp., Sulfolobus spp and thermophilic sulfur-dependent archaeobacteria [structural data reviewed in Sprott, G. D. (1992) J. Bioenergetics and Biomembranes 24: 555–566].

The relative stabilities of ester and ether liposomes prepared by pressure extrusion were compared. These studies showed enhanced stabilities of ether liposomes. The stability of archaeobacterial ether liposomes and their inherent insensitivity to oxidation and esterases make them attractive candidates for many liposome applications.

We claim:

1. A novel polyether lipid of structural formula I

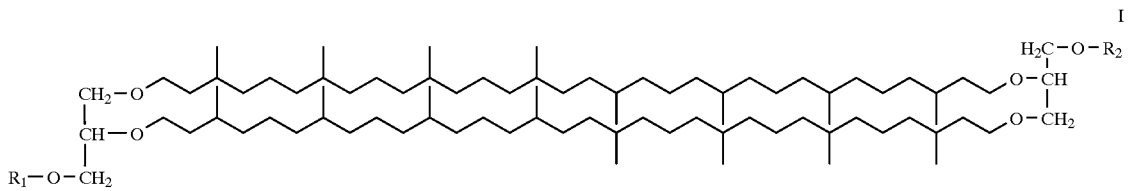

wherein $R_1$ is $\beta$-gal$_f$-, and $R_2$ is $\alpha$-glc$_p$-(1–2)-$\beta$-gal$_f$- in biologically pure form.

2. A novel polyether lipid of structural formula II

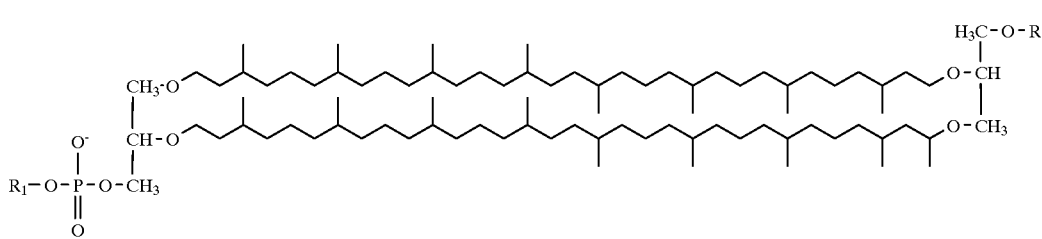

wherein $R_1$ is $(CH_3)_2$-$NC_5O_3H_{10}$- or $(CH_3)_3$-N—$C_5O_3H_{10}$- and
$R_2$ is $\alpha$-glc$_p$- (1–2) -$\beta$-gal$_f$- or
$\beta$-gal$_f$- (1–6) -$\beta$-gal$_f$- or $\beta$-gal$_f$- in biologically pure form.

3. A compound according to claim 2, wherein $R_1$ is $(CH_3)_3$-N—$C_5O_3H_{10}$- and wherein $R_2$ is $\alpha$-glc$_p$-(1–2) -$\beta$-gal$_f$-.

4. A compound according to claim 2, wherein $R_1$ is $(CH_3)_3$-N—$C_5O_3H_{10}$-, and wherein $R_2$ is β-gal$_f$-(1–6)-β-gal$_f$-.

5. A compound according to claim 2, wherein $R_1$ is $(CH_3)_2$-N—$C_5O_3H_{10}$-, and wherein $R_2$ is β-gal$_f$-.

6. A compound according to claim 2, wherein $R_1$ is $(CH_3)_2$-N—$C_5O_3H_{10}$-, and wherein $R_2$ is α-glc$_p$- (1–2)- β-gal$_f$-.

7. A novel polyether lipid of structural formula III

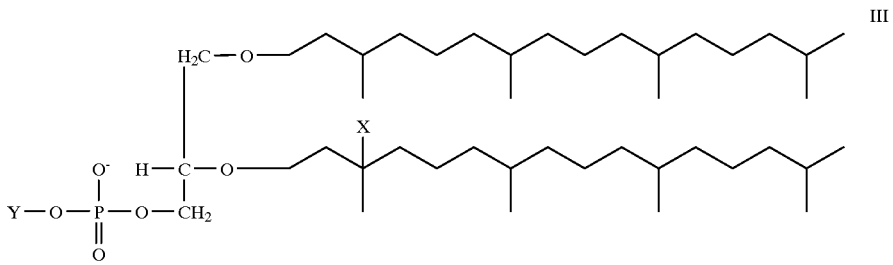

wherein X is —OH, and wherein Y is ethanolamine or glycerol in biologically pure form.

8. A compound according to claim 2, wherein $R^1$ is $(CH_3)_2$ -N—$C_5O_3H_{10}$ - or $(CH_3)_3$-N—$C_5O_3H_{10}$-, and wherein $R_2$ is β-gal$_f$- (1–6)- β-gal$_f$-.

9. A compound according to claim 7, wherein X is OH and Y is ethanolamine.

10. A compound according to claim 7, wherein X is OH and Y is glycerol.

11. A liposome vesicle, the bilayer membrane of which consists essentially of the total polar lipid extract of an archaeobacterium selected from the group consisting of *Methanospirillum hungatei, Methanococcus jannaschii, Methanococcus voltae, Methanosarcina mazei, Methanobrevibacter smithii, Methanosphoera stadtmanae, Methanobacterium espanolae, Thermoplasma acidophilum, Natronobacterium magadii, Methanosaeta concilii*, and mixtures thereof.

12. A liposome according to claim 11, wherein the liposome is a multilamellar liposome.

13. A liposome according to claim 11, wherein the liposome is a unilamellar liposome.

14. A liposome according to claim 13, wherein the archaeobacterium is selected from the group consisting of *Methanococcus voltae, Methanosarcina mazei, Methanococcus jannaschii* and *Methanosaeta concilii*.

15. A liposome according to claim 14, having a mean diameter of <100 nm.

16. A liposome according to claim 15, having a coefficient of correlation of size distributions of between 0.20 and 0.40.

17. A liposome according to claim 11, wherein the archaeobacterium is *Thermoplasma acidophilum*.

18. A liposome according to claim 11, wherein the archaeobacterium is *Methanobrevibacter smithii*.

19. A liposome according to claim 11, wherein the archaeobacterium is *Methanobacterium espanolae*.

20. A liposome according to claim 11, wherein the archaeobacterium is *Methanospirillum hungatei*.

21. A liposome according to claim 11, wherein the archaeobacterium is *Methanosarcina mazei*.

22. A process for the production of unilamellar liposomes from the total polar lipid extract of an archaeobacterium selected from the group consisting of methanogens and thermoacidophiles, comprising (a) subjecting cells of the archaeobacterium to solvent extraction to provide a total polar lipids fraction, (b) adding a suitable detergent, in a molar ratio (detergent:lipid) ranging at least from 10:1 to 30:1, and removing the solvent completely by evaporation, (c) dissolving the resulting detergent/lipid material in a suitable aqueous dialysis buffer to from mixed micelles of lipid and detergent, and (d) subjecting the mixed micelles to controlled dialysis to remove the detergent, and form the liposomes.

23. A process according to claim 22, wherein the molar ratio (detergent:lipid) is about 20:1.

24. A process according to claim 23, wherein the detergent is a non-ionic detergent.

25. A process according to claim 24, wherein the detergent is n-octyl-β-D-glucopyranoside.

26. A process according to claim 22, including the additional step of heat sterilizing the liposomes.

27. A liposome vesicle, the bilayer membrane of which consists essentially of the total polar lipids extract of an archaeobacterium formed by a process according to claim 22.

28. A process for the production of liposomes from the total polar lipid extract of an archaeobacterium selected from the group consisting of methanogens and thermoacidophiles, comprising (a) subjecting cells of the archaeobacterium to solvent extraction to provide a total polar lipids fraction, (b) removing the solvent by evaporation and adding a suitable aqueous extrusion buffer to form a multilamellar liposome emulsion at a pH range of 3.0 to 10.7, and where unilamellar liposomes are required, (c) extruding the multilamellar liposome emulsion at a temperature of 4 to 80° C. under pressure through a membrane of selected pore size to form the unilamellar liposomes.

29. A process according to claim 28, wherein the pore size of the membrane is 50 to 400 nm.

30. A process according to claim 29, wherein step (c), the temperature is ambient.

31. A process according to claim 30, wherein step (b) the pH is about 7.

32. A liposome vesicle, the bilayer membrane of which consists essentially of the total polar lipids of an archaeobacterium formed by a process according to claim 28.

* * * * *

UNITED STATES PATENT AND TRADEMARK OFFICE
CERTIFICATE OF CORRECTION

PATENT NO. : 5,989,587

DATED : November 23, 1999

INVENTOR(S) : G. Dennis Sprott, et al

Page 1 of 2

It is certified that error appears in the above-identified patent and that said Letters Patent is hereby corrected as shown below:

Cover page title ARCHAEU should read ARCHAEA

At column 3-4 in formula II, and at column 27-28 all $CH_2$

At column 1 in title "ARCHAEU "should read --ARCHAEA--

At column 12, line 23, "HKQC" should read --HMQC--

At column 12, line 23, "oherence" should read --coherence--

At column 19, in table 7, heading – missing superscript "PH's" should read -- different PH's[1] --

At column 23, in table 11 the heading "Intemmity[1]" should read -- Intensity[1] --

UNITED STATES PATENT AND TRADEMARK OFFICE
CERTIFICATE OF CORRECTION

PATENT NO. : 5,989,587
DATED : November 23, 1999
INVENTOR(S) : G. Dennis Sprott, et al It is certified that error appears in the above-identified patent and that said Letters Patent is hereby corrected as shown below:

At column 23, in Table 11 the heading "$CF^1$" should read ---$CF^2$--

At column 26, line 60, "Table II" should read --Table 11 --

At Claim 1, column 28, after "ß-gal$f$" insert –isolated--after "in" insert --a --

At Claim 2, column 28, line 55-56, after "ß-gal$f$" insert –isolated--, after "in" insert --a --

At Claim 7, column 29, line 23 after "glycerol" insert --, isolated--, after "in" insert --a --

At Claim 16, column 29, line 50, "claim 15" should read --claim 13--

Signed and Sealed this

Tenth Day of April, 2001

Attest:

NICHOLAS P. GODICI

Attesting Officer     Acting Director of the United States Patent and Trademark Office